United States Patent [19]

Orth et al.

[11] 4,352,287
[45] Oct. 5, 1982

[54] ROTATIONAL VISCOMETER

[75] Inventors: Heinz W. Orth; James W. Sloot, both of Calgary, Canada

[73] Assignee: Dresser Industries, Inc., Dallas, Tex.

[21] Appl. No.: 162,137

[22] Filed: Jun. 23, 1980

[51] Int. Cl.³ .......................................... G01N 11/14
[52] U.S. Cl. ..................................................... 73/60
[58] Field of Search ................................ 73/54, 59, 60

[56] References Cited

U.S. PATENT DOCUMENTS

| 2,553,844 | 5/1951 | Buchdahl et al. | 73/60 |
| 2,812,656 | 11/1957 | Merrill | 73/60 |
| 3,602,035 | 8/1971 | Spohn et al. | 73/59 X |
| 3,875,791 | 4/1975 | Fitzgerald et al. | 73/59 |
| 3,977,234 | 8/1976 | Lynch et al. | 73/53 |
| 4,062,225 | 12/1977 | Murphy, Jr. et al. | 73/60 |
| 4,241,601 | 12/1980 | Pennington et al. | 73/59 |

OTHER PUBLICATIONS

API Recommended Practice, Standard Procedure for Testing Drilling Fluids, Seventh Edition, Apr. 1978.

Primary Examiner—James J. Gill
Attorney, Agent, or Firm—John N. Hazelwood; Peggy L. Smith

[57] ABSTRACT

A microprocessor controlled rotating-cylinder viscometer for measuring the shear stress at a given shear rate of a fluid is disclosed. The fluid is contained between a rotatable outer cylinder and a rotatable inner cylinder. The inner cylinder rotates in response to the torque produced by rotation of the outer cylinder in the fluid. The amount of rotation of the inner cylinder is related to the shear stress of the fluid. A fast slewing accurate motor speed control is provided for maintaining rotation of the outer cylinder at the selected shear rates. An absolute value shaft encoder monitors the amount of rotation of the inner cylinder to obtain the shear stress readings. The steady state value of the shear stress is obtained by averaging a predetermined number of measurements taken over a sample interval to obtain a stress reading. Consecutive readings are compared until the difference between readings in less than ±1°, the current shear stress then taken on the steady state value.

32 Claims, 16 Drawing Figures

FIG. 4  MEMORY AND I/O ASSIGNMENTS

ROM

| ADDRESS | ALLOCATION |
|---|---|
| 000-3CF | PROGRAM MEMORY |
| 3D0-3FF | BCD-7SEG. LOOKUP TABLE |
| 400-7FF | PROGRAM MEMORY |

RAM

| ADRESS | ALLOCATION |
|---|---|
| 00-07 | REGISTERS 0 TO 7 |
| 08-17 | 8 LEVEL STACK |
| 18-1A | KEYBOARD DATA |
| 1B-1D | RPM AND TIME DATA |
| 1E-20 | STRESS AND MESSAGE DATA |
| 21-3E | STRESS STORAGE |
| 40-5D | SPEED STORAGE |
| 5E-7F | SCRATCH PAD MEMORY |

P1 | 7 | 6 | 5 | 4 | 3 | 2 | 1 | 0 |

P10-13  BCD INPUTS
P14-17  BCD AND DIGIT SELECT INPUTS

P2 | 7 | 6 | 5 | 4 | 3 | 2 | 1 | 0 |

P20-22  CHIP SELECT DECODER ADDRESS
P23-24  CONTROL OUTPUTS
P25     1RPM ACTIVATOR

P27     MOTOR ENABLE ACTIVATOR

ROTATIONAL VISCOMETER

BACKGROUND OF THE INVENTION

This invention relates to rotational viscometers for measuring rheometric properties of a fluid. More particularly, this invention relates to a microprocessor controlled rotational type viscometer for automatically and accurately obtaining the steady state shear stress of a fluid at various preselected shear rates.

Properties of fluids, such as the shear stress, shear strength, yield stress, plastic viscosity, etc., are important in many different industries. For example, viscometers are widely used in the drilling industry to measure these properties of drilling fluids that are used to drill oil and gas wells. Information obtained with viscometers is important in controlling the effectiveness of the drilling fluid in, (1) removal of cuttings from the bottom of the hole and carrying them to the surface, (2) holding the cuttings and weight material in suspension when circulation is interrupted, (3) releasing the cuttings and any entrained gases at the surface, (4) transmission of hydraulic horsepower to the drill bit, (5) minimizing annular pressure drops so as to avoid fracturing and the resulting loss of circulation in the uncased hole, (6) maximizing bore hole stability by controlling erosional effects on the well bore while circulating, and (7) reducing to a minimum any adverse effects upon the formation adjacent to the bore hole.

Direct-indicating concentric cylinder rotational viscometers powered by means of an electric motor or hand crank have found wide acceptance in the petroleum industry as an acceptable approach to measuring the viscocity of drilling fluid. In such a viscometer, the drilling mud is contained in the annular space between two cylinders. The outer cylinder or rotor sleeve is driven at a constant rotational velocity or shear rate. Located within the outer cylinder is an inner cylinder. The rotation of the outer cylinder in the mud produces a torque on the inner cylinder. A torsion spring restrains rotational movement of the inner cylinder. A dial scale is attached to the inner cylinder, and with rotation of the inner cylinder, indicates on a fixed pointer the angular displacement of the inner cylinder. The torque produced on the inner cylinder by rotation of the outer cylinder rotates the inner cylinder until the torque on the torsional spring is counter balancing the torque exerted by the fluid. At this point, a reading of the viscosity of the fluid may be taken.

However, direct-indicating rotational viscometers suffer from several problems. Primarily, a high degree of accuracy in shear stress readings is difficult to attain when reading from a scale. Fluctuations in the meter scale about an average position occur as a result of changing physical properties of the fluid and the presence of solid particles in the fluid as the outer cylinder is rotated. As a result, the operator reading the scale must interpolate the average position of the scale. The API recommendation Standard Procedure for Testing Drilling Fluids (APIRP 13B, 7th Edition, April 1978) suggest a that before reading the shear stress at a given shear rate, the dial reading should be allowed to come to a "steady value." Heretofore, rotational viscometers had to depend upon the operator's subjective determination of when a "steady value" has been attained. However, a slow drift in the steady dial reading may occur even with relatively stable readings on the dial, i.e. there are relatively small fluctuations in the dial's position. This drift can be brought about by gradual change in the structure of the fluid. As a result, a quantitative determination of when a steady value or steady state condition of the fluid had been reached is difficult to attain in these prior-art-viscometers.

A further problem in direct-indicating rotational viscometers is the inability of the outer cylinder to change speeds quickly, and at the same time, be capable of maintaining accurate selected shear rate speeds. One such prior-art means for maintaining an accurate shear rate speed in a rotational viscometer is disclosed in U.S. Pat. No. 4,062,225. A phase locked loop (PLL) motor speed control circuit is shown for controlling the shear rate speed of the rotated outer cylinder. Attached to the motor shaft is a high inertia flywheel which functions to dampen out speed variations of the motor at the selected shear rates. Unfortunately, the inertia of the flywheel does not permit a rapid change in the motor speed as the shear rate is changed.

This inability to rapidly change speed becomes especially significant when the viscometer is measuring the "Gel" strength of the fluid. As recommended at Page 6 of the API bulletin identified above, when measuring "Gel" strength, the fluid is mixed at high speed for 10 seconds, stopped for 10 seconds and then run at 3 RPM. The maximum reading is recorded and process of mixing, stopping and running at a low RPM is repeated. For this procedure, it is implied that following the mixing step, the outer cylinder is immediately stopped to allow the fluid to reform. This would not be possible with a motor speed control system utilizing a flywheel to attain high accuracy shear rate control. The inertia of the flywheel requires a significant amount of time for the rotating outer cylinder to come to a stop.

Accordingly, it would be advantageous to provide a rotating type viscometer in which the shear rate speeds can be controlled to a high degree of accuracy, but at the same time, permit rapid changes in the rotation of the outer cylinder. It would also be advantageous to provide a viscometer that could determine quantitatively the steady state condition of the shear stress at each selected shear rate to achieve a high degree of accuracy in shear rate measurements. It would also be advantageous to provide a viscometer that could automatically and accurately measure the shear stress of a fluid at each of a pre-selected number of shear rates to obtain data values which will permit the piece-wise linear approximation to the shear stress profile of the fluid, particularly in the region of actual shear rate conditions encountered in the annulus of a well bore.

SUMMARY OF THE INVENTION

In accordance with this invention, a rotational concentric cylinder viscometer for measuring the steady state shear stress of a fluid at a given shear rate is provided. The fluid, whose viscosity is to be measured, is contained between a rotatable outer cylinder and a spring loaded rotatable inner cylinder such that rotation of the outer cylinder produces a torque acting through the fluid on the inner cylinder thereby causing the inner cylinder to rotate. The total amount of rotation of the inner cylinder is related to the shear stress of the fluid as measured at the shear rate.

A microprocessor unit is provided to input and output data signals that will select the various shear rates of rotation of the outer cylinder, and measure the resulting amount of rotation of the inner cylinder at each selected shear rate. A system clock provides several system clock signals to control the various functions and timing of the viscometer. A shear rate controller responds to the system clock and the shear rate selecting data from the microprocessor to rotate the outer cylinder at the selected constant angular velocity. An angular position indicator comprising an absolute value shaft encoder outputs a digital Gray code that is used to indicate the angular position of the inner cylinder.

A function selector means comprising a manually actuated keyboard is connected to the microprocessor input data lines for inputting both the mode of operation of the microprocessor and for inputting the various pre-selected shear rates at which the outer cylinder is to be rotated. A display means is provided to display both a measured shear stress and the angular velocity of the outer cylinder at which the display shear stress was measured.

The shear rate controller that controls the rate of rotation of the outer cylinder includes a programmable frequency divider that responds to the shear rate selecting data from the microprocessor to produce a phase detector clock signal. The phase detector clock signal is produced by dividing the feedback frequency signal obtained from a speed encoder connected to the outer cylinder. The speed encoder is an optical incremental encoder mechanically connected to the outer cylinder for rotation therewith. A motor drive means responds to the phase detector clock signal to generate the excitation signal to the motor that rotates the outer cylinder. This motor drive means includes a phase detector that responds to the system clock and the phase detector clock signal to generate a phase error signal that indicates the phase difference between the phase detector clock signal and a reference signal. Also included is an amplifier that filters and amplifies the phase error signal to produce the motor excitation signal. The motor used to rotate the outer cylinder is a DC-motor of the ironless armature type.

In another aspect of the invention, a method for obtaining the steady state shear stress of a fluid at a selected shear rate using the microprocessor controlled rotating-cylinder viscometer is also disclosed. The method comprises the steps of changing the outer cylinder rotational speed to a selected shear rate, determining a current average value for the angular position of the inner cylinder from a predetermined number of position measurements taken at a predetermined sample rate. The difference between a current average value and the last obtained average value is then obtained. The result is then compared with a predetermined number of degrees to determine if the steady state condition of shear stress has been attained. If not, the process of obtaining a current average value is repeated until the difference is less than or equal to the predetermined number of degrees, at which point the current average value is taken as the steady state shear stress.

In another aspect of the invention, a method for obtaining the instant "GEL" and 10 minute "GEL" using the microprocessor controlled rotating cylinder viscometer is also disclosed. The method comprises the programmed steps of mixing, waiting the appropriate delay time, and starting the outer cylinder at 3 RPM during which the highest shear stress reading obtained in an interval of 20 seconds, corresponding to one complete revolution of the outer cylinder, is stored for later recall.

In yet a further aspect of the invention, a method for obtaining the shear stress profile (shear stress vs. shear rate) of a fluid using the microprocessor controlled rotating-cylinder viscometer is disclosed. The method for determining the steady state shear stress at a selected shear rate is repeated for each of the pre-selected shear rates until all readings have been obtained.

BRIEF DESCRIPTION OF THE DRAWINGS

The novel features believed characteristic of this invention are set forth in the appended claims. The invention and advantages thereof may best be understood by reference to the following detailed description of the illustrative embodiments read in conjunction with the accompanying drawings which form a part of this specification, and in which corresponding numerals indicate corresponding parts.

In the Drawings:

FIG. 4 is a tabular listing of the program memory allocation for microprocessor 10 of the present invention.

DETAILED DESCRIPTION OF THE PREFERRED EMBODIMENTS OF THE PRESENT INVENTION

Figure 1:
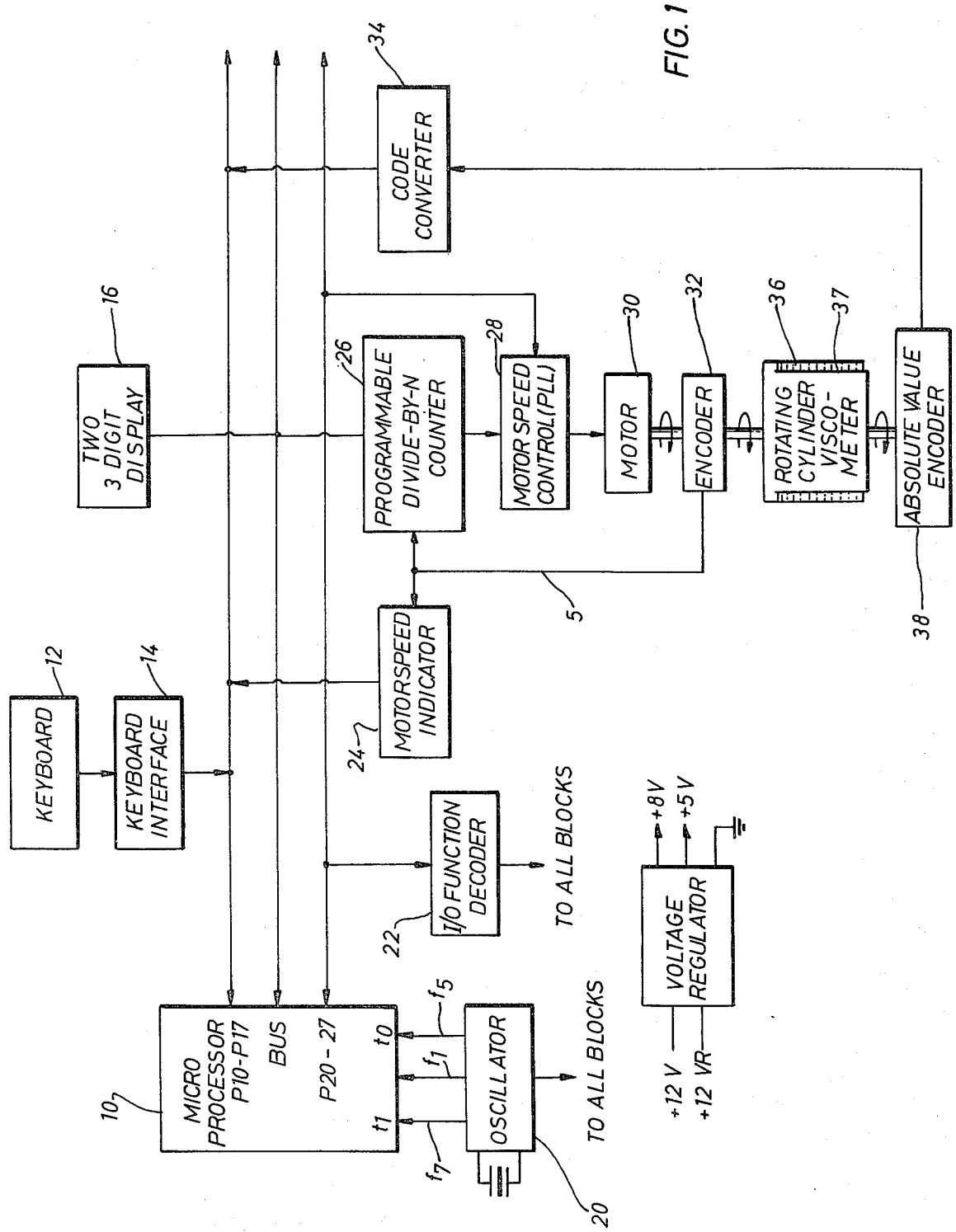
FIG. 1 is a block diagram representation of the microprocessor controlled rotating-cylinder viscometer of the present invention.

Referring to the figures and first to FIG. 1, a block diagram of the rotational concentric cylinder viscometer of the present invention is shown. A microprocessor 10 functions to control the operations of the rotating viscometer, and to measure the resulting angular rotation of the inner cylinder indicative of the shear stress of the fluid at a given shear rate. The various elements of the viscometer are connected to the microprocessor 10 by way of three data buses, I/O ports P1 (P10-P17) and P2 (P20-P27), and data bus BUS. In the preferred embodiment of the present invention, microprocessor 10 is manufactured and sold by Intel Corporation as its MCS 8749 Microcomputer.

A crystal controlled system clock 20 is provided to generate various frequencies used to control the functions and timing of the viscometer. In the preferred embodiment, system clock 20 outputs seven frequencies illustrated in the following Table 1:

TABLE 1

| F | Frequency (Hz) |
|---|---|
| 1 | 4,194,304 |
| 2 | 2,097,152 |
| 3 | 16,384 |
| 4 | 512 |
| 5 | 4 |
| 6 | 2 |
| 7 | 1 |

Frequency f1 is supplied to the microprocessor 20 for its internal timing, f2 is supplied to the programmable keyboard/display interface 72 (FIG. 3), f3 is supplied to the keyboard encode chip 82 (FIG. 3), f4 is supplied to the motor speed control 28, f5 is supplied to the microprocessor 10 for digit display purposes, f6 is supplied to the motor speed indicator 24 and f7 is supplied to the elapsed timer contained in microprocessor 10.

Command control data is outputted by the microprocessor 10 to initiate various sequences in the elements of the viscometer or to cause data to be applied to the data buses. Operation of the microprocessor controlled viscometer is initiated from a keyboard assembly 12 having 18 buttons. Two of the 18 buttons are used to switch the power on and off to the circuits. The remaining 16 keys are labeled as follows: 10 of the keys contain the digits 0-9, one each of the remaining 6 keys are respectively labeled STORE, RECALL, ERASE, ENTER, AUTO, and GEL. The 10 keys marked with digits 0-9 are used to input numeric data to select the speed for the various shear rates, and to select the memory locations in conjunction with the "STORE" key. The "RECALL" key is used in conjunction with a series of numeric actuated keys to display a stored value. Any speed selected and inputted to the microprocessor 20 from the keyboard and not ENTERed can be erased with the "ERASE" without interfering with the previous selected speed. Automatic programs can be terminated by actuating the "ERASE" key. The functions performed by the "ERASE" key are as follows: It clears entries during a keyboard input sequence; it clears any "Err" messages; it causes an exit from the "GEL" routine while counting elapsed time; it causes an exit from the "GEL" routine during the 20-sec comparison interval; it causes an exit from the "AUTO" sequence during settling time after speed change; it causes an exit from "RECALL"; it causes an exit from "STORE" with no effect on memory contents; it causes an exit during the 10 second mixing interval; and it causes a jump to the calibration routine if depressed during power-up.

All selected speeds have to be entered with the "ENTER" key. The functions of the "ENTER" key are as follows: It loads the keyboard input data into the programmable divider 26; it starts the comparison routine in "GEL" at the displayed elapsed time; and it causes a return to the main program after completion of the calibration routine. All keyboard actuated numbers are displayed, with the keyboard indicator light on, until it is entered into memory. At that time, the display 16 will indicate the actual speed of the rotating outer cylinder and the resulting steady state shear stress. Any invalid number inputted will display an error "Err". The function of the "AUTO" and the "GEL" keys, will be described in detail below.

The viscometer of the present invention may be operated either in an automatic or a manual mode. In the automatic mode, "AUTO", the steady state shear stress for each of a predetermined number of preselected shear rates will be obtained and stored in memory. This data can then be used to obtain a piece-wise linear approximation to the viscosity profile of the fluid at various shear rates. In order to perform the automatic determination of the shear stress, the keyboard 12 key labeled "AUTO" must be depressed.

When the viscometer is operated in a manual mode, it is possible to preselect the speed at which the outer cylinder is to be rotated by inserting the desired rotation rate via the numbered keys and depressing the "ENTER" key. The outer cylinder will begin to rotate at the inputted speed. When the operator is satisfied that the steady state value of the shear stress has been attained, depressing the "STORE" button and a numeric button corresponding to a memory location will cause the microprocessor 10 to read both the actual speed of the outer cylinder, via motor speed indicator 24, and the resulting shear stress. This data will be stored in the memory location corresponding to the numeric key depressed after the "STORE" key. During the manual mode of operation, the measured speed and shear stress data are outputted to two 3-digit displays 16.

Still referring to FIG. 1, control of the rotation of the outer cylinder 36 is achieved through the combination of microprocessor 10, programmable divide-by-N counter 26, motor speed control 28 and the DC-motor 30. In particular, the pre-selected or manually entered shear rate data is outputted by microprocessor 10 as a divide factor N to programmable divide counter 26. Counter 26 divides a feedback frequency signal 5 outputted by an optical incremental encoder 32 that is coupled to the rotation of motor 30. The rate of rotation of motor 30 controls the frequency of the feedback frequency signal 5 that is inputted both to the programmable divide counter 26 and to the motor speed indicator 24. The function of motor speed indicator 24 is to produce a digital code word that indicates the actual rotational speed of the motor that is occurring. The output of motor speed indicator 24 is applied as data input to the microprocessor 10, and is read under control of the micro processor.

The output of programmable divide-by-N counter 26 is applied to motor speed control 28 where it is compared with a reference frequency supplied by system clock 20. For the presently preferred embodiment the reference clock signal is f4, 512 Hz. The phase difference between the reference frequency and the output of the programmable counters 26 is a phase error signal that is filtered and amplified to produce the excitation signal to DC-motor 30. Rotation of the output shaft of motor 30 is reflected as a feedback frequency signal 5. When the feedback frequency signal 5 reaches the proper frequency, as determined by the divide factor N and the reference frequency from system clock 20, the excitation signal to DC-motor 30 will remain constant to cause motor 30 to run at the desired velocity. Variations of the motor 30 speed will be reflected as a variation in the feedback frequency signal 5. These variations will produce an appropriate change in the motor excitation signal to bring the motor speed back to the desired setting.

In the presently preferred embodiment of the invention, the DC-motor 30 is a permanent magnet DC-motor having an armature wound on a hollow non-magnetic core. Motors such as these having no magnetic material in the armature or rotor are known as "Ironless motors." A suitable motor of the ironless type is manufactured and sold by Interelectric Corporation of Switzerland as a Maxom DC-motor series 2332 and by Dr. Faulhaber Company of Germany as series 3557. An ironless motor is desirable because of its low inertia and fast acceleration. These features enable the motor to achieve a fast reacting precision motor control, and a short settling time.

Figure 2:
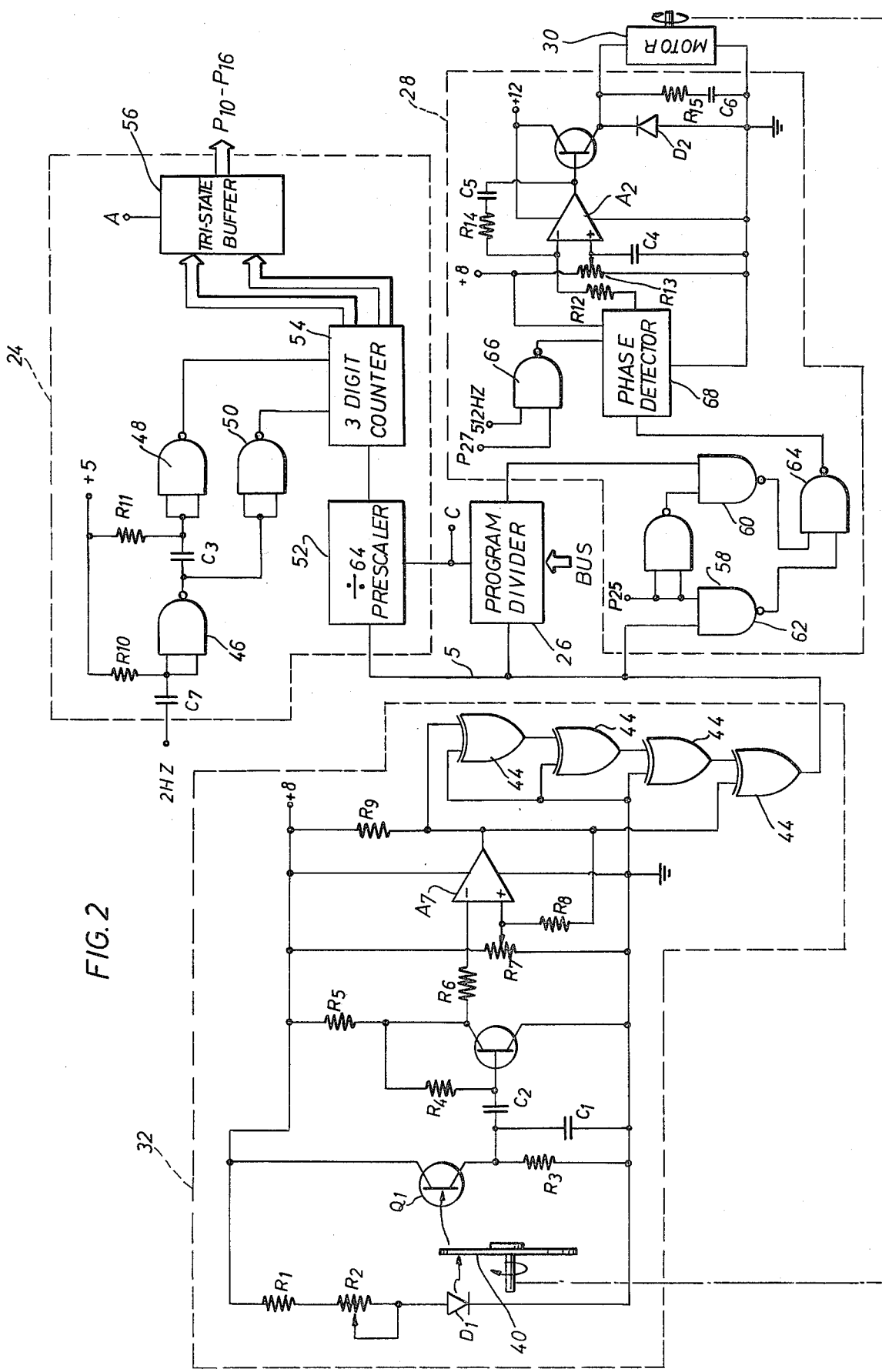
FIG. 2 is a circuit diagram of the phase locked loop controller of the present invention that controls the rate of rotation of the outer cylinder.

Referring now to FIGS. 1 and 2, the concentric rotating cylinders 36 respond to rotation of the DC-motor 30 to produce a corresponding rotation in the shaft of the inner cylinder. This angular rotation is monitored by absolute value shaft encoder 38 that outputs a digital code word indicative of the actual angular position of the inner cylinder. This digital data is inputted to a code converter 34 whose output is coupled onto one of the microprocessor 10 data buses, P10–P17. In the presently preferred embodiment, absolute value shaft encoder 38 outputs a 9-bit Gray code where only one bit line is permitted to change per interval of angular rotation of the encoder shaft. The position encoder 38 is graduated from −9° to +350° deflection. The code converter 34 converts the Gray code of encoder 38 into its BCD equivalent values. Code converter 34 consists of a ROM having the BCD equivalent codes stored in memory locations that are addressed by the output code words from the encoder 38. Each output code word from encoder 30 serves as a unique address to the code converting ROM.

To perform the code conversion, a 9-bit address to the code converting ROM contained in converter 34 is generated by the encoder 38. The most significant bit of the 10-bit address to the ROM is inputted from the microprocessor 10 on the P23 data bus line. Under program control, microprocessor 10 causes I/O decoder 80 to generate the strobe D to multiplex onto data bus lines P10–P17 two BCD digits of the three BCD digits that represent the angle of the inner cylinder's shaft. Data bus P23 is then set and strobe D generated to output from the code converting ROM the third BCD digit along with the + or − sign for the angle. The encoder disk 35 of encoder 38 is properly etched to produce the Gray code. To produce the electrical signals to read the etched disk 35, the present invention uses a Texas Instruments light emitting diode array T1L 49 and a photosensitive transistor array T1L629.

Turning now to FIG. 2, the motor speed indicator 24, programmable divider counters 26 and motor speed control 28 are illustrated in more detail. The encoder 32 consists of a rotatable disc 40 having slits or means therein for permitting the passage of light from light emitting diode D1 to reach the base of light sensitive transistor Q1. The output of transistor Q1 is amplified and applied to comparator A1 to produce a digital signal at the input of exclusive OR gates 44. The output of exclusive OR gates 44 comprises the feedback frequency signal 5. For the preferred embodiment, encoder 32 produces 3840 pulses per revolution on the output shaft of outer cylinder 36. At a rotor speed of 600 RPM, encoder 32 produces a frequency of 76,800 pulses per second.

As previously discussed, the feedback frequency signal 5 is applied to programmable divider 26 to produce the phase frequency signal on its output. This signal is applied as one input to two input NAND gate 60. Inverter 58 responds to a control signal from data bus P25 to provide the other input to NAND gate 60. Control signal P25 functions to select the phase frequency clock from programmable divider 26 as the input signal to phase detector 68 for all rotor speeds above 1 RPM. When a rotor speeds of 1 RPM is desired, the microprocessor 10 outputs a control signal on P25 to select the feedback frequency signal 5 as the frequency to be applied directly to phase detector 68 by way of NAND gates 62 and 64.

As illustrated in FIG. 2, NAND gates 58, 60, 62 and 64 function as an AND/OR gate to select either the output of the programmable divider 26 or the feedback frequency signal 5 as the input clock signal to phase detector 68 depending upon the state of data bus line P25. The divide parameter N from the divide-by-N counter 26 is supplied to the programmable divider 26 from the microprocessor 10 BUS. Programmable divider 26 is manufactured and sold by Intel Corporation as a model 8253 divide-by-N counter. Prescaler counter 52 which forms part of the motor speed indicator 24 is contained in the Intel 8253 chip.

Also inputted to the motor speed control circuit 28 is a second control signal, P27, from microprocessor 10. This signal enables the phase detector 68 to generate an excitation signal to the motor 30 to cause it to begin rotation. When data bus line P27 is not active, motor 30 will not rotate. When enabled by P27, the 512 Hz frequency signal f4 from the system clock 20 is applied to phase detector 68 which, for the preferred embodiment of the present invention, is manufactured and sold by Motorola Incorporated as a phase/frequency detector MC14568. This particular phase detector contains a divide by 4 internal counter to reduce the 512 Hz reference signal down to 128 Hz. The phase detector 68 produces an error signal representative of the phase difference between the signal from the encoder 32 divided by the division ratio N, and the 128 Hz reference signal. This error signal is filtered and amplified by amplifier A2 and power amplifier Q3 to provide the excitation signal to the motor. It should be clear that the values of the various circuit components, voltages, and their manufacturer type numbers depicted in FIG. 2 and described above will vary depending upon the intended use. In a presently preferred embodiment use in connection with a phase locked loop control system to control the speed of rotation of motor 30, Table 2 below sets out exemplary values which have been found satisfactory.

TABLE 2

| REFERENCE | VALUE (ohms) | REFERENCE | TYPE or VALUE |
|---|---|---|---|
| R1 | 120 | C1 | 820pf |
| R2 | 1K,VAR | C2,C6 | .1 f |
| R3 | 47K | C3,C7 | .001 f |
| R4,R6,R12 | 100K | C4 | 1 f |
| R5,R9 | 1K | C5 | 10 f |
|  |  | D1 | OPTRON INC. 81355 |
| R7, R13 | 100K,VAR | D2 | 55T |
| R8 | 330K | Q1 | OPTRON INC. 81355 |
| R10, R11 | 10K | Q2 | 2N4123 |
| R14 | 6.8K | Q3 | MJE6044, 2N6388 |
| R15 | 39 | A1 | LM311, MLM311 (National) |
|  |  | A2 | LM358, MLM358 (Motorola) |

Still referring to FIG. 2, the motor speed indicator 24 for determining the actual speed of rotation of the motor 30 is shown. The feedback frequency signal 5 is applied to a divide by 64 pre-scaler 52 to reduce the frequency generated by encoder 32. This reduced frequency is applied to a 3-digit BCD counter 54 that is periodically cleared by the 2 Hz reference signal f6 from the system clock 20. Counter 54 is manufactured and sold by Motorola as model MC14553. The 3-digit counter 54 functions to generate a 3-digit BCD code equal to the number of pulses produced in a time interval of one second, and multiplexes each digit sequentially onto its output. The multiplexed output of the 3-digit counter 54 is applied to a tri-state buffer circuit 56 that responds to function strobe A from decoder 22 to apply the BCD digits onto the microprocessor bus P10–P16. Also strobed onto the data bus lines P10–P16 are the digit selection bits that indicate which of the three BCD digits from counter 54 is currently being multiplexed into the buffer 56. For the presently preferred embodiment, buffer 56 is a Texas Instruments tri-state buffer model SN74LS244. The control signal A is generated in response to function control data outputted by microprocessor 10 when a reading of the speed of rotation of the outer cylinder 36 is desired.

Figure 3:
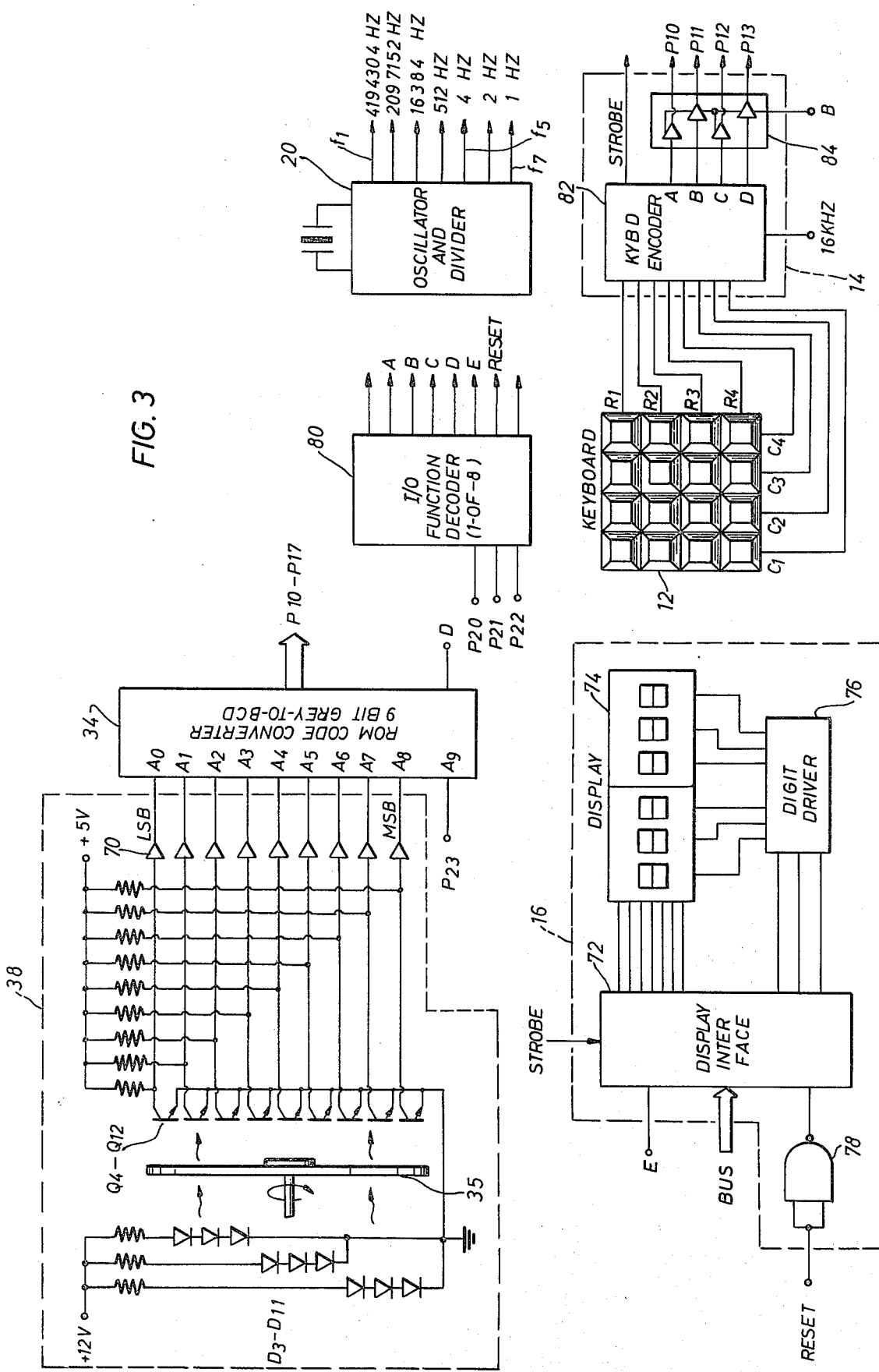
FIG. 3 is a circuit diagram of various blocks illustrated in FIG. 1 including the inner cylinder position indicating means, the I/O function decoder and the keyboard entry to the microprocessor.
Figure 5:
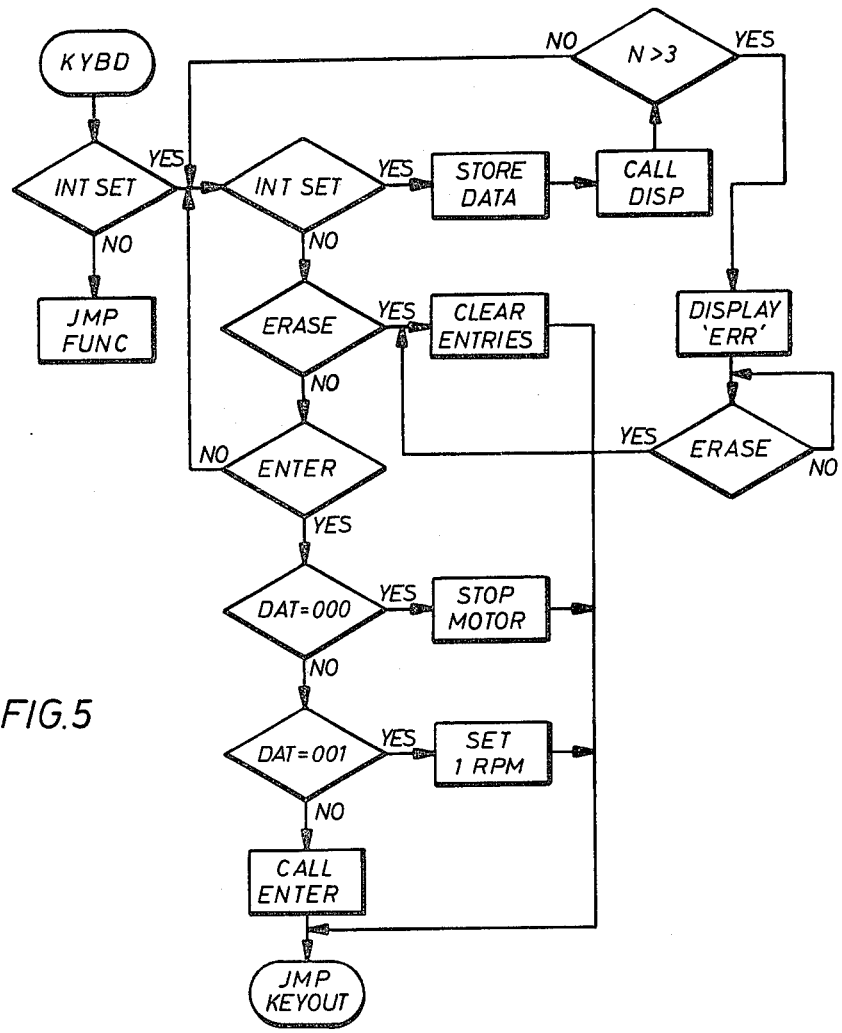
FIGS. 5-16 are software flow diagrams for the various routines for the programmed microprocessor 10.
Figure 6:
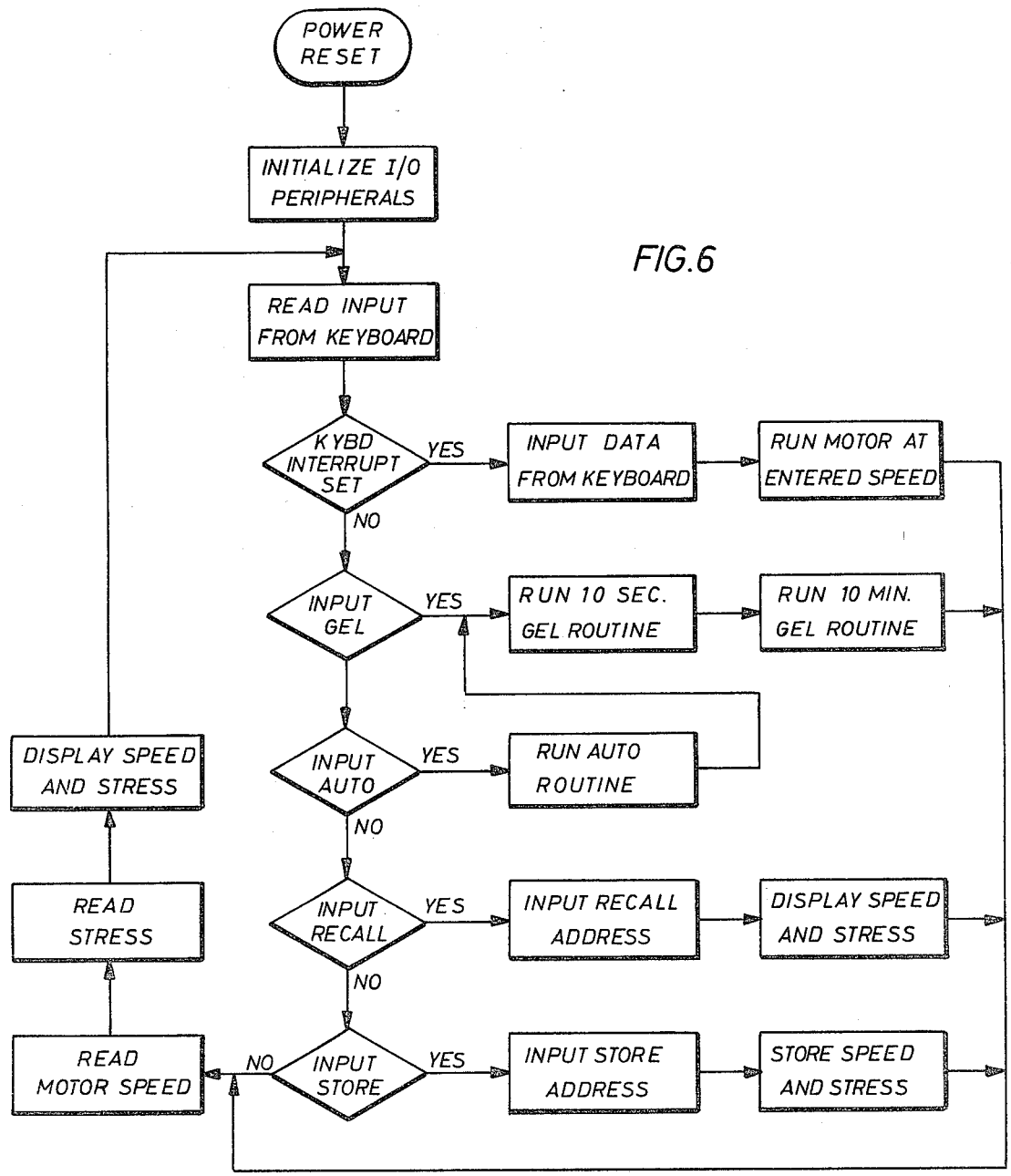
Figure 7:
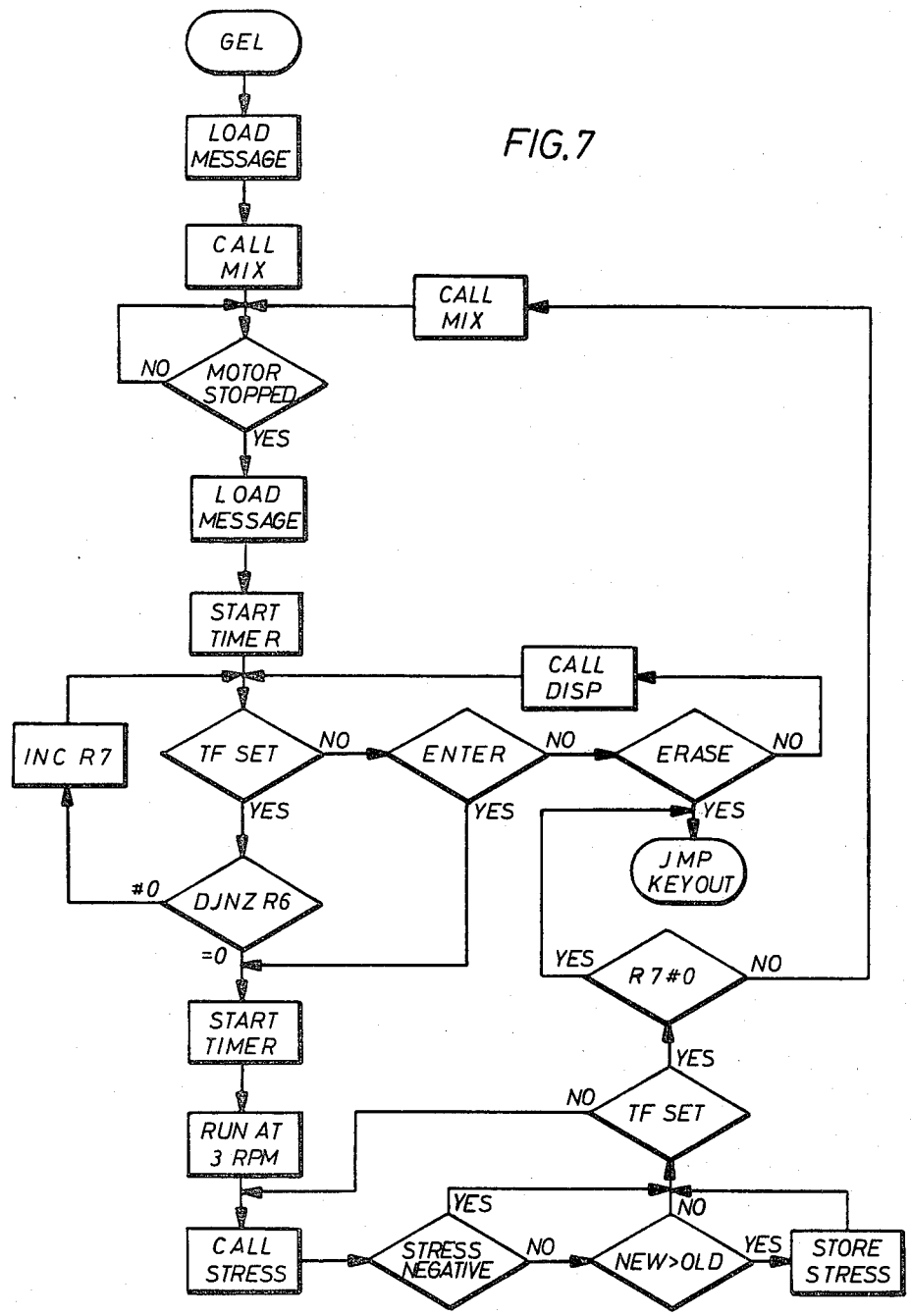
Figure 8:
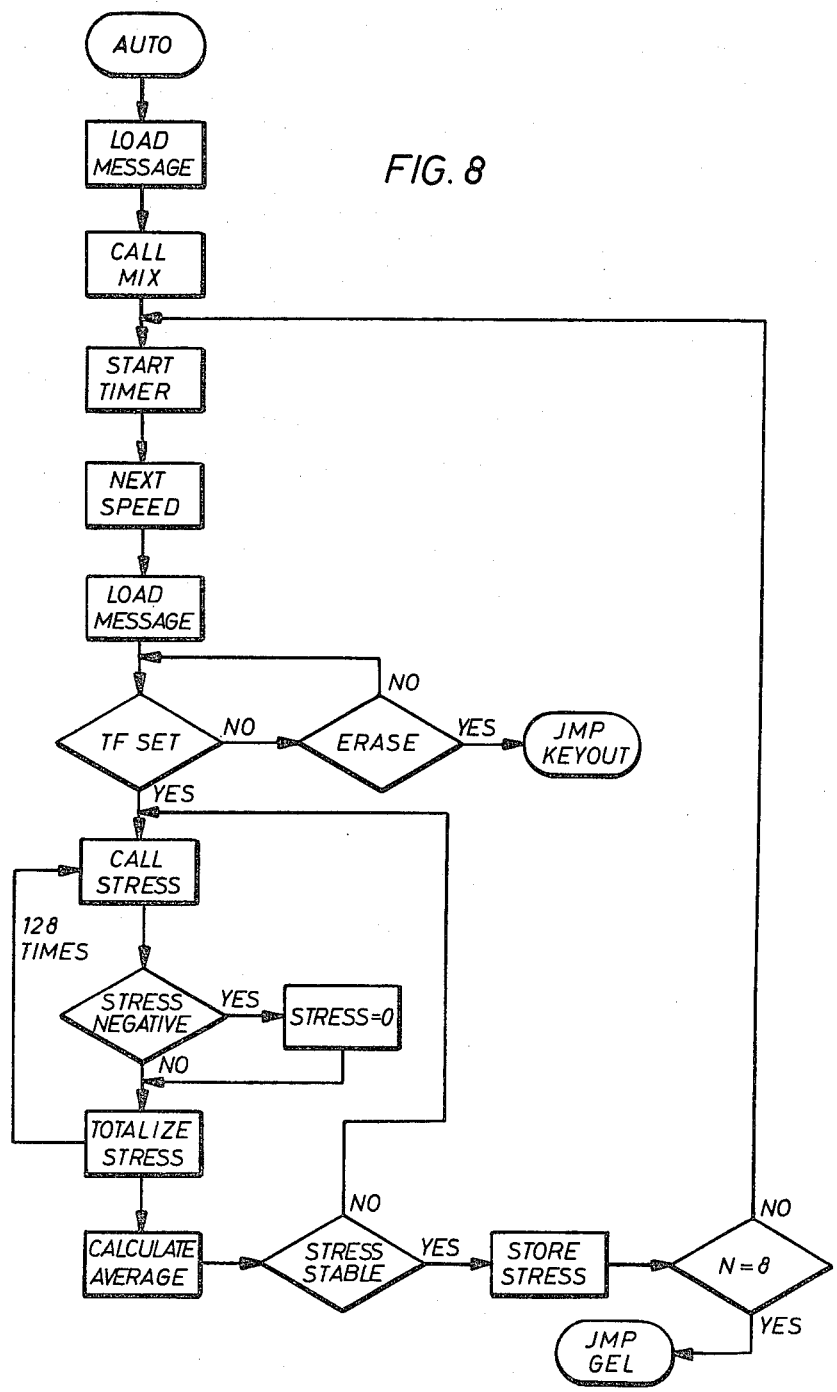
Figure 9:
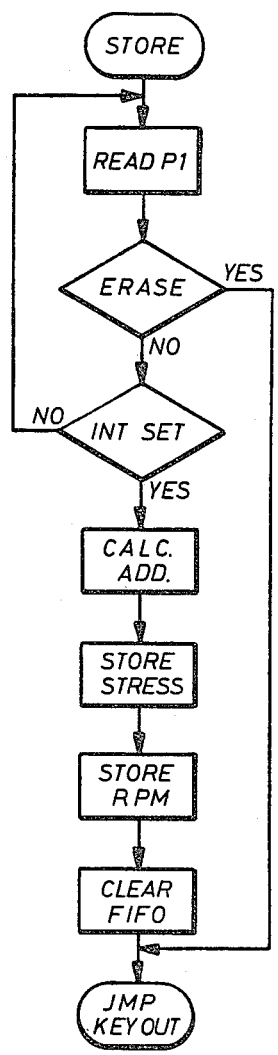
Figure 10:
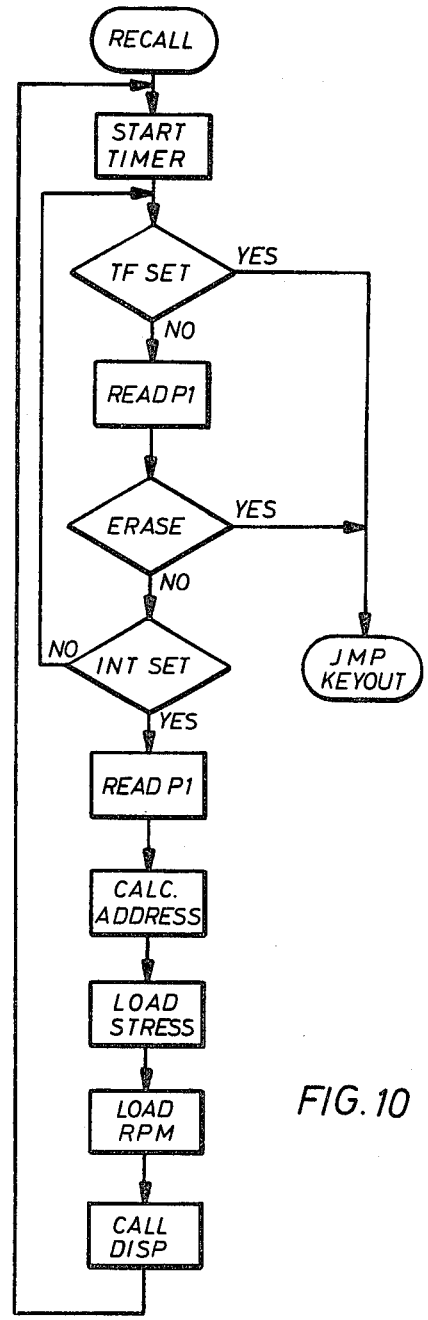
Figures 11, 12:
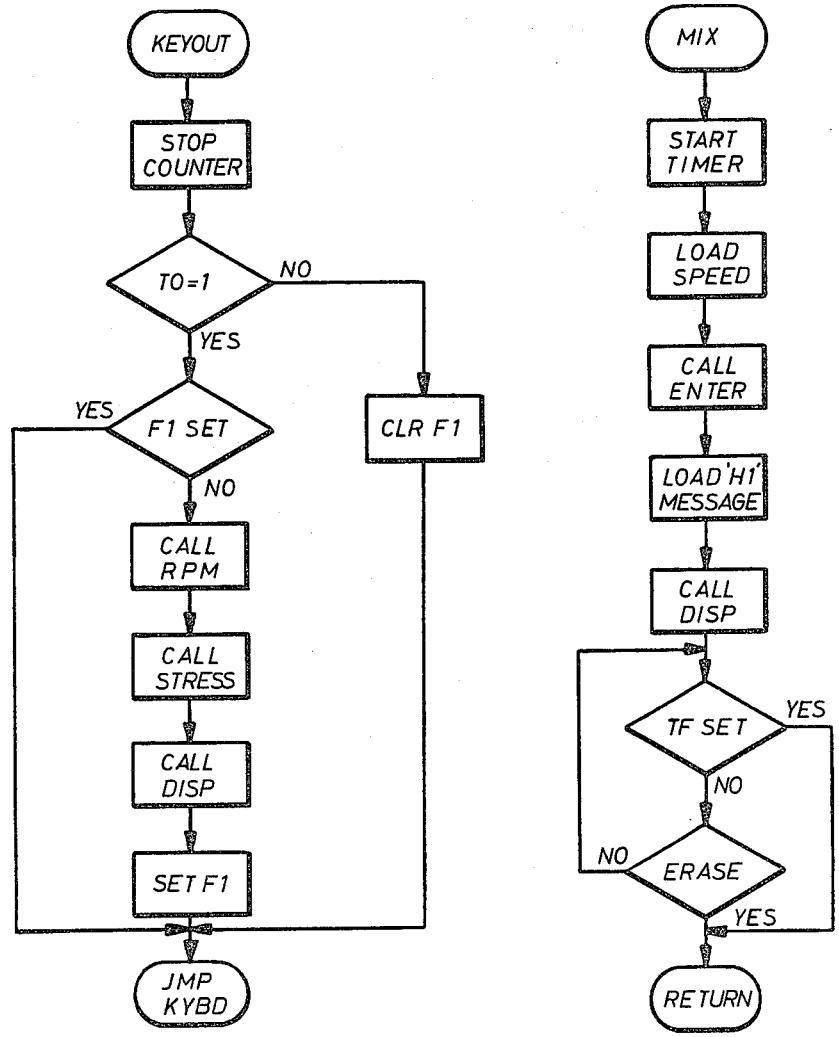
Figures 13, 14:
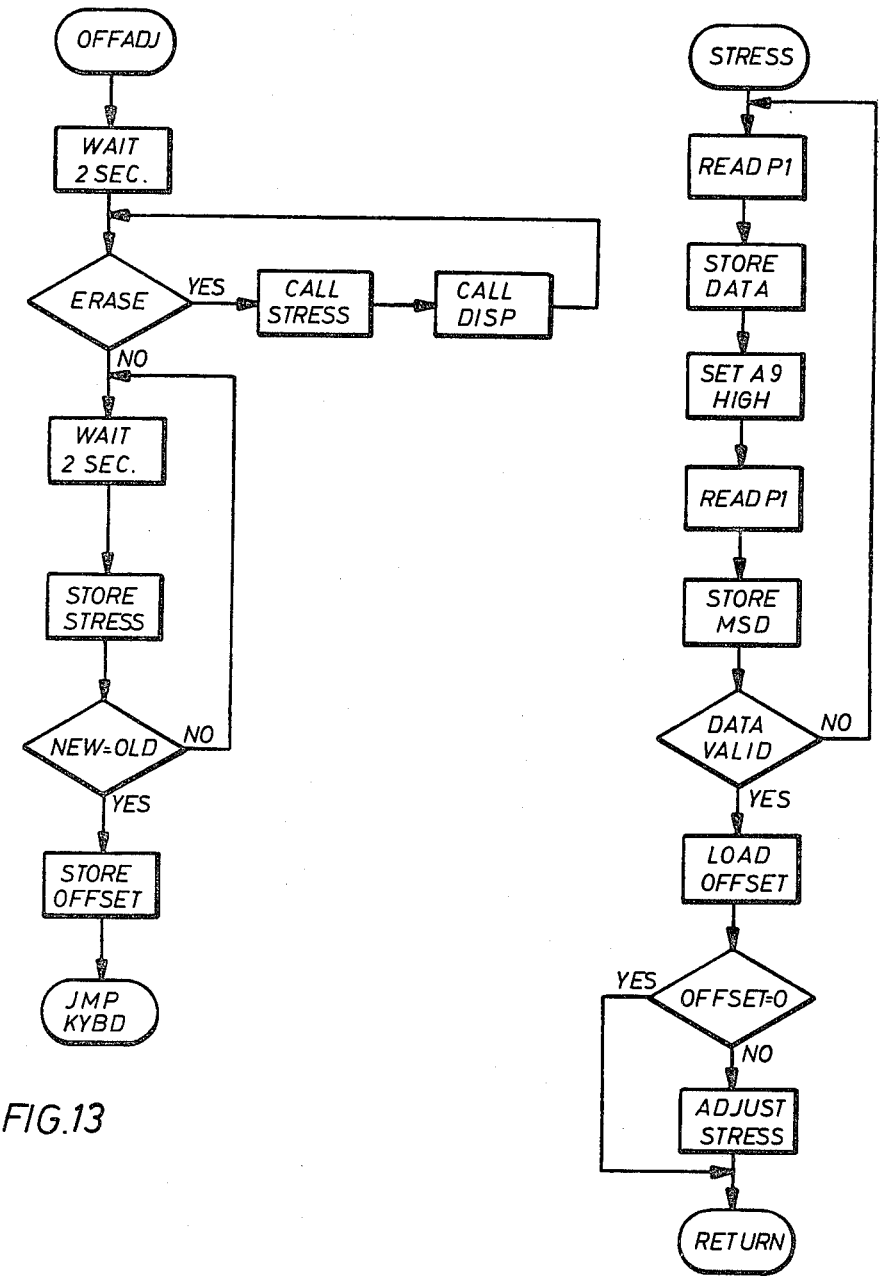
Figures 15, 16:
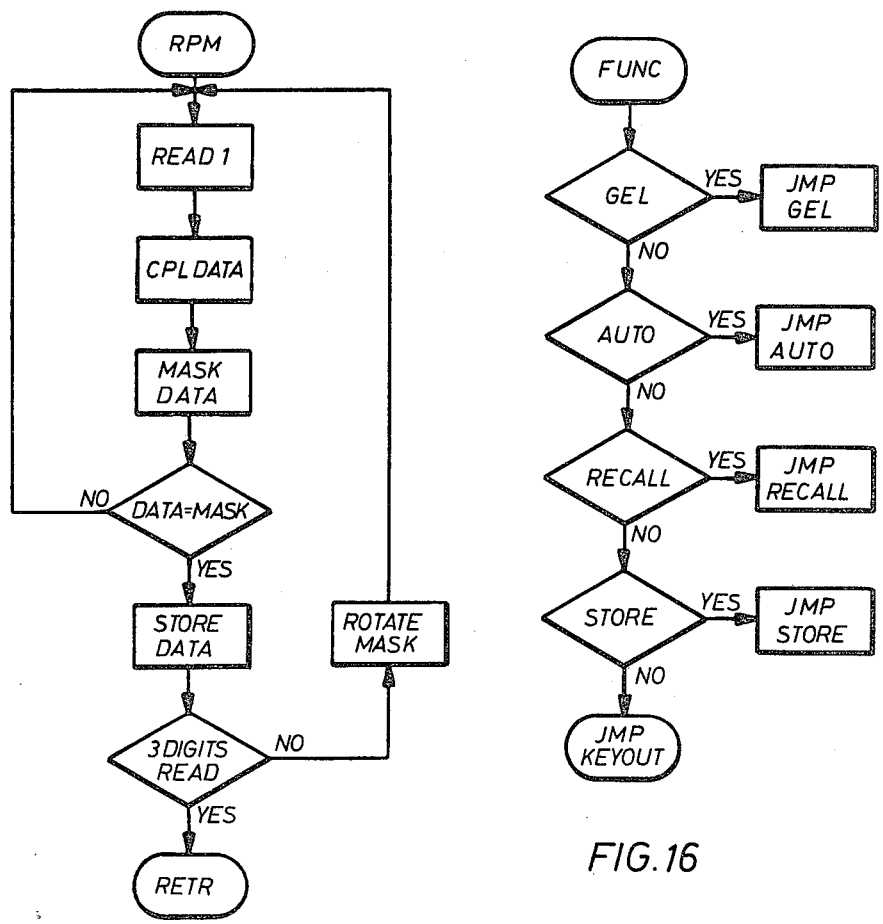

Turning now to FIG. 3 in which various functions illustrated in FIG. 1 are illustrated in more particular detail, the absolute value shaft encoder 38 is shown responding to the rotatable inner cylinder 37 of the concentric rotating cylinders. The encoder 38 functions in a similar manner to the optical encoder 32 in that light emitting diodes D3–D11 are used to produce light that is applied to the bases of transistors Q4–Q12 through a disc that rotates with the shaft of the inner cylinder 37. Each output of transistors Q4–Q12 is applied to a respective buffer gate 70 to produce the 9-bit digital code representative of the angular position of the inner cylinder 37. As previously mentioned, the 9-bit Gray code word is applied to code converter 34 for conversion to BCD digits that are applied to the microprocessor data bus lines P10–P17. The data from the encoder 38 is applied to the bus through the code converter 34 in response to function strobe D outputted by the I/O function decoder 22.

The I/O function decoder chip 22 which generates the various function strobe signals is of a 1-of-8 decoder that responds to the microprocessor 10 data bus lines P20–P22 to produce eight strobes used to control various sequencies and to enable data to be inputted to the microprocessor 10 data buses. For the preferred embodiment, decoder 22 is manufactured and sold by Intel Corporation as model 8205. Also illustrated in FIG. 3 is the system clock 20. It will be appreciated by those of ordinary skill in the art that the basic reference frequency produced by a crystal controlled oscillator may be divided down by counters to produce the reference frequencies illustrated. Accordingly, the circuits for this function are not shown and discussed herein.

Further illustrated in FIG. 3 is the keyboard 12 consisting of 16 keys that are used to input the data to the microprocessor 10 needed to operate the viscometer. The output from the various keys are applied to the keyboard encoder 82. Encoder 82 responds to the the 16 KHz reference frequency f3 from the system clock 20 to produce the 4-bit binary code eventually applied through the buffer gates 84 to the microprocessor 10 input data bus lines P10–P13. Function strobe B enables gate 84 to apply the 4-bit code words onto the data lines. Also produced in the keyboard encoder 82 is a strobe signal that is applied to the display interface 72 which generates an interrupt request signal to microprocessor 10. The strobe signal is only produced when one of the numeric keys is depressed. The actuation of one of the mode control keys to the microprocessor 10 does not produce an immediate response from the microprocessor. Rather, the internal software routines will periodically read the output from the keyboard buffer gates 84 and determine if any of the function keys have been depressed.

Still referring to FIG. 3, the two 3-digit displays 16 are shown diagrammatically as composed of 7-segment display digits 74 that respond to digital driver 76 and display interface 72. The digits to be displayed in the digits 74 are loaded from the microprocessor 10 BUS lines into the display interface 72 on the occurrence of the control signal E from the I/O function decoder 22. The various digits to be displayed are serially loaded into display interface 72 which time multiplexes the digits onto the control lines to the digits of display 74. In this manner, the data stored in display interface 72 appears to be continuously displayed by the display unit 74. The presently preferred embodiment has used an Intel Corporation 8279 display chip for display 16.

As previously mentioned, the present invention is able to determine the steady state value for the shear stress at each of the preselected rotor speeds. Shortly after application of power to the electronic circuits, the microprocessor 10 measures the angular position of the inner cylinder at zero speed to determine if an offset error is present. This offset error is used to correct all further angular position measurements. Upon entry into the automatic mode by microprocessor 10, the outer cylinder is rotated at 700 RPM for a period of 10 seconds to mix the fluid. Mixing is required to cause a breakdown of all particle bonds for particles suspended in the fluid. At the end of the 10 second interval, the outer cylinder is then rotated at 600 RPM a period of 2 seconds to allow for the speed of the outer cylinder 36 to stabilize and become phase locked to the fixed reference signal from the system clock 20. Readings of the angular deflection as reflected from absolute value shaft encoder 38 are then taken at a sample rate of 128 samples/second for one second.

Characteristic of all concentric rotating cylinder viscometers is the presence of fluctuations in the angular position of the inner cylinder 37 due to random variations in the torque transmitted by the fluid to the inner cylinder 37. The magnitude and rate of the fluctuations may vary from fluid sample to fluid sample depending on the amount and size of the solid particles present. For the present invention, it is important that the sample rate of angular position readings of the inner cylinder 37 be at least two times the maximum rate of fluctuations present in the angular position of the inner cylinder. As the readings are taken, they are consecutively totalized until all of the readings have been taken. Then, the total is divided by the number of samples taken, 128, to give an average angular deflection of the inner cylinder position for that one second measuring interval. The presence of solid particles in the fluid being tested can exert intermittent or irregular forces on the cylinder thus causing the cylinder to oscillate about a mean angular position. The averaging sequence eliminates the need for a mental averaging by the operator to obtain this mean, and thereby reduces the possibility of an error in the reading.

Many fluids exhibit thixotropic properties and require a certain time period for particle bonds to reform after a reduction in shear rate. After all bonds that can exist at a particular shear rate have reformed, the shear stress will reach an equilibrium value and a reading may be taken. For this reason, the averaging sequence is performed again after a two second time interval. The next average value thus obtained is compared to the previous average value, and if the two valves are within plus or minus one degree ($\pm 1°$) of each other, the current average value is accepted as the true equilibrium or steady state reading. If the current average value differs in magnitude by more than one degree from the previous average value, another two second time interval elapses and the averaging process is again repeated. This procedure continues until the difference between the present and previous readings are within the desired range.

After the steady state reading has been determined, that reading, along with the shear rate at which it was obtained, is stored in a memory location for later recall and display. In one embodiment of the present invention, the rotational speeds of 600, 300, 200, 100, 60, 30, 15, 6 and 3 RPMs are recommended to obtain shear stress readings that will permit the piece-wise linear approximation of the shear stress versus shear rate curve, and allow the operator to make calculations on certain rheometric properties of the fluid. The various shear rates to obtain the shear stress profile would have been inputted into the microprocessor 10 prior to initiating the automatic mode of operation. The above described procedure for obtaining the steady state shear stress at a shear rate would then be repeated for each of the preselected and inputted shear rates until the measurements of shear stress at each of the speeds has been obtained.

In the automatic mode, after all of the preprogrammed shear rate readings have been measured and recorded, the microprocessor 10 proceeds to the GEL mode. This GEL mode is also separately selectable by the operator by depressing the button on the keyboard marked "GEL." Upon initial entry into the GEL mode, the outer cylinder 36 is rotated at 700 RPM for a period of 10 seconds. Again to mix the fluid under test and to break down particle bonds that give the fluid thixotropic properties. After the mixing period, the outer cylinder rotation is stopped and the elapsed time counter interval to microprocessor 10 is initiated to generate the elapsed time. The microprocessor 10 internal elapse time counter is incremented once every second by f7, and upon reaching 10 seconds, the outer cylinder 36 is rotated at 3 RPM. Immediately as the outer cylinder 36 starts to rotate at 3 RPM, readings of the angular displacement of the inner cylinder 37 are taken in rapid succession for a period of 20 seconds corresponding to one complete revolution of the outer cylinder 36. During this 20 second time period, the largest value is retained, and after the 20 second period, this maximum value is stored in an operator specified addressable memory location for later recall. This stored reading corresponds to the inital GEL strength of the fluid under test. The fluid is then mixed as before and then the same sequence of measurements occur after a second time period of 10 minutes. The elapse timer can be interrupted manually by depressing the ENTER button and with this manual override, any time GEL, up to 600 seconds can be taken. When all measurements are completed, the microprocessor 10 exits the GEL routine and leaves the outer cylinder rotating at 3 RPM with the display showing the speed and corresponding shear stress reading.

Referring now to FIGS. 5–16, software flow diagrams for various functions performed by the present invention are shown. These flow diagrams illustrate the functions performed by microprocessor 10 in response to the various modes of operation keyed from keyboard 12. The following is an assembler language listing of the microprocessor 10 program that implements the flow diagrams of FIGS. 5–16. It will be appreciated by those skilled in the art that other routines other than those illustrated and described herein could be programmed into microprocessor 10 and achieve the same results.

```
1     TITLE( 8749 2K RHEOMETER PROGRAM V2
2     MACROFILE   DEBUG XREF PAGEWIDTH (80) NOGEN
3     WRITE       MACRO PORT2,DBUS
4                 MOV A, #PORT2
5                 OUTL P2,A
6                 MOV A, #DBUS
7                 OUTL BUS,A
8                 ENDM
9     PREP        MACRO AND,OR,PORT
10                ANL P2,#AND
11                ORL P2,#OR
12                MOV A,#PORT
13                OUTL BUS,A
14                ENDM
15    TAB7        EQU 0ECH
16                MOV A,#0GH          ;RESET 8279
17                OUTL P2,A
18                NOP
19                ANL P2,#00H
20                MOV R0,#18H         ;CLEAR RAM 18 to 7F
21                MOV R7,#68H
22                CLR A
23    CLEAR:      MOV @R0,A
24                INC R0
25                DJNZ R7,CLEAR
26                WRITE 15H, 06H      ;SET KYDB/DISP MODE
31                MOV A,#35H
32                OUTL BUS,A          ;PROGRAM 8279 CLOCK
33                MOV A,#0C3H
34                OUTL BUS,A          ;CLEAR ALL IN 8279
35                MOVA,#80H
36                MOV T,A
37                STRT T
38                JTF +4
39                JMP −2
40                STOP TCNT
41                WRITE 1BH, 16H      ;PROGRAM 8253 CNT 0
46                MOV A,#56H
47                OUTL BUS,A          ;PROGRAM 8253 CNT 1
48                MOV A,#0B5H
49                OUTL BUS,A          ;PROGRAM 8253 CNT 2
50                WRITE 0BH,40H       ;LOAD CNT 1
55                WRITE 13H,00H
60                MOV A,#01H
```

| | | -continued | |
|---|---|---|---|
| 61 | | OUTL BUS,A | |
| 62 | | MOV A,#02H | |
| 63 | | OUTL P2,A | ;SET FOR KYBD INPUT |
| 64 | | JMP OFFADJ | |
| 65 | KYBD: | ANL P2,#0A0H | |
| 66 | | ORL P2,#02H | |
| 67 | | JNI FUNC | |
| 68 | | MOV R7,#04H | |
| 69 | STAT: | JNI DATIN | |
| 70 | | MOV R0,#18H | |
| 71 | | ANL P2,#0E0H | |
| 72 | | ORL P2,#42H | |
| 73 | | IN A,P1 | ;INPUT KYBD DATA |
| 74 | | ANL A,#0FH | |
| 75 | | XCH A,@R0 | |
| 76 | | INC R0 | |
| 77 | | XCH A,@R0 | |
| 78 | | INC R0 | |
| 79 | | MOV @R0,A | |
| 80 | | MOV R0,#18H | |
| 81 | | MOV R1,#1BH | |
| 82 | | MOV R6,#03H | |
| 83 | | MOV A,@R0 | |
| 84 | | MOV @R1,A | |
| 85 | | INC R0 | |
| 86 | | INC R1 | |
| 87 | | DJNZ R6,$−4 | |
| 88 | | CALL DISP | |
| 89 | | CALL CLRFIF | |
| 90 | | DJNZ R7,STAT | |
| 91 | | JMP ERROR | |
| 92 | DATIN: | ANL P2,#0E0H | |
| 93 | | ORL P2,#02H | |
| 94 | | IN A,P1 | |
| 95 | | ANL A,#0FH | |
| 96 | | MOV R5,A | |
| 97 | | XRL A,#0AH | |
| 98 | | JZ ERASE | ;TEST FOR 'ERASE' |
| 99 | | MOV A,R5 | |
| 100 | | XRL A,#0BH | |
| 101 | | JZ ENTIN | ;TEST FOR 'ENTER' |
| 102 | | JMP STAT | |
| 103 | ERASE: | CLR A | |
| 104 | | MOV R0,#18H | |
| 105 | | MOV R7,#06H | |
| 106 | | MOV @R0,A | |
| 107 | | INC R0 | |
| 108 | | DJNZ R7,$−2 | |
| 109 | | JMP KEYOUT | |
| 110 | ERROR: | MOV R0,#1BH | ;LOAD 'ERR' MESSAGE |
| 111 | | IMP (13H, 13H) | |
| 112 | | MOV @R0, #M | |
| 113 | | INC R0 | |
| 114 | | ENDM | |
| 119 | | MOV @R0,#0FH | |
| 120 | | CALL DISP | |
| 121 | | ANL P2,#0E0H | |
| 122 | | ORL P2,#02H | |
| 123 | | IN A,P1 | |
| 124 | | ANL A,#0FH | |
| 125 | | XRL A,#0AH | |
| 126 | | JZ ERASE | ;TEST FOR 'ERASE' |
| 127 | | JMP $−7 | |
| 128 | ENTIN: | MOV R0,#1AH | ;TOTAL KYDB REGISTER |
| 129 | | MOV A,@R0 | |
| 130 | | DEC R0 | |
| 131 | | ADD A,@R0 | |
| 132 | | MOV R7,A | |
| 133 | | DEC R0 | |
| 134 | | ADD A,@R0 | |
| 135 | | JZ MOTOFF | |
| 136 | | DEC A | |
| 137 | | JNZ G0ENT | |
| 138 | | MOV A,R7 | |
| 139 | | JNZ GOENT | |
| 140 | | MOV a,#0A0H | |
| 141 | | OUTL P2,A | |
| 142 | | MOV R0,#18H | |
| 143 | | CLR A | |
| 144 | | MOV @R0,A | |
| 145 | | INC R0 | |
| 146 | | MOV @R0,A | |

-continued

| | | | |
|---|---|---|---|
| 147 | | INC R0 | |
| 148 | | MOV @R0,A | |
| 149 | | JMP KEYOUT | |
| 150 | MOTOFF: | CLR A | ;TURN MOTOR OFF |
| 151 | | OUTL P2,A | |
| 152 | | JMP KEYOUT | |
| 153 | GOENT: | CALL ENTER | |
| 154 | | JMP KEYOUT | |
| 155 | FUNC: | IN A,P1 | ;CHECK KYBD FUNCTIONS |
| 156 | | ANL A,#0FH | |
| 157 | | MOV R5,A | |
| 158 | | XRL A,#0CH | |
| 159 | | JNZ $+4 | |
| 160 | | JMP GEL | |
| 161 | | MOV A,R5 | |
| 162 | | XRL A,#0DH | |
| 163 | | JNZ $+4 | |
| 164 | | JMP AUTO | |
| 165 | | MOV A,R5 | |
| 166 | | XRL,#0EH | |
| 167 | | JNZ $+4 | |
| 168 | | JMP RECALL | |
| 169 | | MOV A,R5 | |
| 170 | | XRL A,#0FH | |
| 171 | | JNZ $+4 | |
| 172 | | JMP STORE | |
| 173 | | JMP KEYOUT | |
| 174 | GEL: | CALL GMESS | |
| 175 | | CALL MIX | |
| 176 | | MOV R4,#0F6H | ;R4=CNT START CODE |
| 177 | | MOV R5,#26H | ;R5=STORAGE ADDRESS M |
| 178 | | MOV R6,#01H | ;R6=NO. OF TF OVERFLO |
| 179 | | MOV R7,#00H | ;R7=100's of SEC CNTR |
| 180 | STOPMO: | CLR A | |
| 181 | | OUTL P2,A | |
| 182 | | MOV A,#0FEH | |
| 183 | | MOV T,A | |
| 184 | | STRT CNT | |
| 185 | | MOV A,R5 | |
| 186 | | MOV R0,A | |
| 187 | | CLR A | |
| 188 | | MOV @R0,A | ;CLEAR STORAGE MEMORY |
| 189 | | DEC R0 | |
| 190 | | MOV @R0,A | |
| 191 | | DEC R0 | |
| 192 | | MOV @R0,A | |
| 193 | | JTF $+4 | |
| 194 | | JMP $−2 | |
| 195 | | STOP TCNT | |
| 196 | | CALL GMESS | |
| 197 | COUNT: | MOV A,R4 | |
| 198 | | MOV T,A | |
| 199 | | STRT CNT | ;START TIMER |
| 200 | TFTEST: | JTF LOOPS | |
| 201 | | MOV A,#02H | |
| 202 | | OUTL P2,A | |
| 203 | | IN A,P1 | |
| 204 | | ANL A,#0FH | |
| 205 | | MOV R3,A | |
| 206 | | XRL A,#0BH | ;TEST FOR 'ENTER' |
| 207 | | JNZ $+4 | |
| 208 | | JMP GOGEL | |
| 209 | | MOV A,R3 | |
| 210 | | XRL A,#0AH | ;TEST FOR 'ERASE' |
| 211 | | JZ GELOUT | |
| 212 | | MOV A,T | |
| 213 | | CPL A | |
| 214 | | ADD A,R4 | |
| 215 | | CPL A | |
| 216 | | MOV R2,A | |
| 217 | | MOV R1,#00H | |
| 218 | | MOV R0,#1BH | |
| 219 | TENS: | MOV A,R2 | |
| 220 | | CPL A | ;CONVERT TIMER VALUE |
| 221 | | ADD A,#0AH | ;TO 2 BCD NUMBERS |
| 222 | | JC ONES | |
| 223 | | INC R1 | |
| 224 | | CPL A | |
| 225 | | MOV R2,A | |
| 226 | | JPM TENS | |
| 227 | ONES: | MOV A,R2 | |
| 228 | | MOV @R0,A | |

| | | -continued |
|---|---|---|
| 229 | | INC R0 |
| 230 | | MOV A,R1 |
| 231 | | MOV @R0,A |
| 232 | | INC T0 |
| 233 | | MOV A,R7 |
| 234 | | MOV @R0,A |
| 235 | | CALL DISP |
| 236 | | JMP TFTEST |
| 237 | LOOPS: | DEC R6 |
| 238 | | MOV A,R6 |
| 239 | | JZ GOGEL |
| 240 | | INC R7 |
| 241 | | JMP COUNT |
| 242 | GOGEL: | STOP TCNT |
| 243 | | MOV A,#0ECH |
| 244 | | MOV T,A |
| 245 | | STRT CNT |
| 246 | | MOV A,R5 |
| 247 | | ADD A,#1FH |
| 248 | | MOV R0,A |
| 249 | | MOV R1,A |
| 250 | | MOV @R0,#0EH ;LOAD 'G-N' MESSAGE |
| 251 | | DEC R0 |
| 252 | | MOV @R0,#0AH |
| 253 | | DEC R0 |
| 254 | | MOV A,R1 |
| 255 | | JB0 $+6 |
| 256 | | MOV @R0,#02H |
| 257 | | JMP $+4 |
| 258 | | MOV @R0,#01H |
| 259 | | MOV R0,#18H |
| 260 | | MOV R3,#02H |
| 261 | | MOV @R0,#03H ;LOAD 003 RPM |
| 262 | | INC R0 |
| 263 | | CLR A |
| 264 | | MOV @R0,A |
| 265 | | INC R0 |
| 266 | | MOV @R0,A |
| 267 | | MOV R0,#1BH |
| 268 | | DJNZ R3,$−9 |
| 269 | | CALL ENTER |
| 270 | | CALL DISP |
| 271 | MAGCOM: | CALL STRESS |
| 272 | | MOV R0,#20H ;PREVENT NEG READINGS |
| 273 | | MOV A,@R0 |
| 274 | | XRL A,#0AH |
| 275 | | JZ MAGOUT |
| 276 | | MOV A,R5 |
| 277 | | MOV R1,A |
| 278 | | MOV A,@R1 |
| 279 | | MOV R3,A ;R3=OLD DATA |
| 280 | | MOV R0,#20H |
| 281 | | MOV A,@R0 |
| 282 | | MOV R2,A ;R2=NEW DATA |
| 283 | | CALL COMP |
| 284 | | JF1 MAGOUT ;F1=[R3 R2] |
| 285 | | JNZ STOMAX ;[A=0] = [R3=R2] |
| 286 | | CLR C |
| 287 | | DEC R0 |
| 288 | | DEC R1 |
| 289 | | MOV A,@R1 |
| 290 | | DEC R1 |
| 291 | | SWAP A |
| 292 | | ADD A,@R1 |
| 293 | | MOV R3,A |
| 294 | | MOV A,@R0 |
| 295 | | DEC R0 |
| 296 | | SWAP A |
| 297 | | ADD A,@R0 |
| 298 | | MOV R2,A |
| 299 | | CALL COMP |
| 300 | | JF1 MAGOUT |
| 301 | | JNZ STOMAX |
| 302 | | JMP MAGOUT |
| 303 | STOMAX: | CALL STODAT ;STORE NEW DATA |
| 304 | MAGOUT: | JTF AGAIN |
| 305 | | MOV A,#82H |
| 306 | | OUTL P2,A |
| 307 | | IN A,#82H |
| 308 | | ANL A,#0FH |
| 309 | | XRL A,#0AH ;TEST FOR 'ERASE' |
| 310 | | JNZ MAGCOM |

-continued

| | | | |
|---|---|---|---|
| 311 | | JMP GELOUT | |
| 312 | AGAIN: | MOV A,R7 | |
| 313 | | JNZ GELOUT | |
| 314 | | CALL GMESS | |
| 315 | | CALL MIX | |
| 316 | | MOV R4,#9CH | ;RESET PARAMETERS |
| 317 | | MOV R5,#23H | |
| 318 | | MOV R6,#06H | |
| 319 | | JMP STOPMO | |
| 320 | GELOUT: | STOP TCNT | |
| 321 | | CLR F1 | |
| 322 | | JMP KEYOUT | |
| 323 | AUTO: | CALL AUMESS | |
| 324 | | CALL MIX | |
| 325 | | MOV R4,#08H | |
| 326 | | MOV R6,#0D4H | ;START OF SPEED DATA |
| 327 | LOAD: | MOV A,#0FEH | |
| 328 | | MOV T,A | ;START 2 SEC TIMER |
| 329 | | STRT CNT | |
| 330 | | MOV R0,#1AH | |
| 331 | | MOV R1,#1DH | |
| 332 | | MOV R7,#03H | |
| 333 | | MOV A,R6 | |
| 334 | | MOVP3 A,@A | ;LOAD SPEED DATA |
| 335 | | MOV @R0,A | |
| 336 | | MOV @R1,A | |
| 337 | | DEC R0 | |
| 338 | | DEC R1 | |
| 339 | | INC R6 | |
| 340 | | DJNZ R7,$−7 | |
| 341 | | MOV A,R4 | |
| 342 | | INC A | |
| 343 | | RL A | |
| 344 | | ADD A,R4 | |
| 345 | | ADD A,#41H | |
| 346 | | MOV R1,A | |
| 347 | | MOV R0,#1BH | |
| 348 | | MOV R7,#03H | |
| 349 | | MOV A,@R0 | |
| 350 | | MOV @R1,A | |
| 351 | | INC R0 | |
| 352 | | INC R1 | |
| 353 | | DJNZ R7,$−4 | |
| 354 | | CALL ENTER | |
| 355 | | CALL AUMESS | |
| 356 | | CALL DISP | |
| 357 | | MOV A,#82H | |
| 358 | | OUTL P2,A | |
| 359 | | CLR A | |
| 360 | | MOV R7,#04H | ;CLEAR RAM 7AH TO 7DH |
| 361 | | MOV R0,#7AH | |
| 362 | | MOV @R0,A | |
| 363 | | INC R0 | |
| 364 | | DJNZ R7,$−2 | |
| 365 | RUN: | JTF STEP | |
| 366 | | IN A,P1 | ;TEST FOR ERASE |
| 367 | | ANL A,#0FH | |
| 368 | | XRL A,#0AH | |
| 369 | | JNZ RUN | |
| 370 | | JMP KEYOUT | |
| 371 | STEP: | STOP TCNT | |
| 372 | | MOV R7,#80H | |
| 373 | | SEL RB1 | |
| 374 | | CLR A | |
| 375 | | MOV R4,A | |
| 376 | | MOV R5,A | |
| 377 | | MOV R0,#20H | |
| 378 | | SEL RB0 | |
| 379 | BCDHEX: | CALL STRESS | |
| 380 | | MOV R0,#20H | ;PREVENT NEG READINGS |
| 381 | | MOV A,@R0 | |
| 382 | | XRL A,@9AH | |
| 383 | | JNZ $+8 | |
| 384 | | CLR A | |
| 385 | | MOV @R0,A | |
| 386 | | DEC R0 | |
| 387 | | MOV @R0,A | |
| 388 | | DEC R0 | |
| 389 | | MOV @R0,A | |
| 390 | | SEL RB1 | |
| 391 | | MOV A,#0BBH | |
| 392 | | MOV T,A | |

-continued

| | | |
|---|---|---|
| 393 | STRT T | |
| 394 | JTF $+4 | |
| 395 | JMP $-2 | |
| 396 | STOP TCNT | |
| 397 | CLR C | |
| 398 | MOV A,@R0 | |
| 399 | MOV R2,A | |
| 400 | RL A | |
| 401 | RL A | |
| 402 | MOV R3,A | |
| 403 | RL A | |
| 404 | RL A | |
| 405 | RL A | |
| 406 | MOV R2,A | |
| 407 | ADD A,R3 | |
| 408 | MOV R3,A | |
| 409 | MOV A,R2 | |
| 410 | RL A | |
| 411 | ADD A,R3 | |
| 412 | MOV @R0,A | |
| 413 | JNC $+4 | |
| 414 | INC R5 | |
| 415 | CLR C | |
| 416 | MOV A,R7 | |
| 417 | RL A | |
| 418 | MOV R3,A | |
| 419 | RL A | |
| 420 | RL A | |
| 421 | ADD A,R3 | |
| 422 | MOV R7,A | |
| 423 | ADD A,R6 | |
| 424 | ADD A,@R0 | |
| 425 | JNC $+4 | |
| 426 | INC R5 | |
| 427 | CLR C | |
| 428 | ADD A,R4 | |
| 429 | JNC $+4 | |
| 430 | INC R5 | |
| 431 | CLR C | |
| 432 | MOV R4,A | ;R4 CONTAINS HEX SUM |
| 433 | SEL RB0 | ;R5 CONTAINS OVERFLOW |
| 434 | DJNZ R7,$+4 | |
| 435 | JMP $+4 | |
| 436 | JMP BCDHEX | |
| 437 | SEL RB1 | ;CALC AVERAGE VALUE |
| 438 | CLR F0 | |
| 439 | CLR C | |
| 440 | MOV A,R5 | |
| 441 | RLC A | |
| 442 | MOV R5,A | |
| 443 | MOV A,R4 | |
| 444 | JB7 $+4 | |
| 445 | JMP $+5 | |
| 446 | MOV A,R5 | |
| 447 | INC A | |
| 448 | MOV R5,A | |
| 449 | MOV R0,#7CH | ;DETERMINE IF SYSTEM |
| 450 | MOV R1,#7BH | ;WAS IN EQUILIBRIUM |
| 451 | JNC $+6 | |
| 452 | MOV @R1,#01H | |
| 453 | JMP $+4 | |
| 454 | MOV @R1,#00H | |
| 455 | MOV A,@R0 | |
| 456 | XRL A,R5 | |
| 457 | JZ EQCARR | |
| 458 | DEC R1 | |
| 459 | MOV A,R5 | |
| 460 | ADD A,#01H | |
| 461 | JNC $+6 | |
| 462 | MOV @R1,#01H | |
| 463 | JMP $+4 | |
| 464 | MOV @R1,#00H | |
| 465 | XRL A,@R0 | |
| 466 | JZ EQCARR | |
| 467 | MOV A,R5 | |
| 468 | CPL A | |
| 469 | ADD A,#01H | |
| 470 | CPL A | |
| 471 | MOV R7,A | |
| 472 | JNC $+6 | |
| 473 | MOV @R1,#00H | |
| 474 | JMP $+6 | |

| | | |
|---|---|---|
| 475 | | INC R1 |
| 476 | | MOV A,@R1 |
| 477 | | DEC R1 |
| 478 | | MOV @R1,A |
| 479 | | MOV A,R7 |
| 480 | | XRL A,@R0 |
| 481 | | JZ EQCARR |
| 482 | UNSTAB: | MOV A,R5 |
| 483 | | MOV @R0,A |
| 484 | | MOV R1,#7BH |
| 485 | | INC R0 |
| 486 | | MOV A,#R1 |
| 487 | | MOV @R0,A |
| 488 | | MOV A,#0FEH |
| 489 | | MOV T,A |
| 490 | | STRT CNT |
| 491 | | SEL RB0 |
| 492 | | JMP RUN |
| 493 | EQCARR: | MOV R0,#7DH |
| 494 | | MOV R1,#7AH |
| 495 | | MOV A, @R0 |
| 496 | | XRL A, @R1 |
| 497 | | DEC R0 |
| 498 | | JNZ UNSTAB |
| 499 | | MOV A, @R1 ;DATA ACCEPTED |
| 500 | | CPL A |
| 501 | | JB0 $+4 |
| 502 | | CPL F0 |
| 503 | | CLR C ;CONVERT HEX TO BCD |
| 504 | | MOV R0,#20H |
| 505 | | MOV $7,#00H |
| 506 | | MOV @R0,#00H |
| 507 | NSD: | MOV A,R5 |
| 508 | | CPL A |
| 509 | | ADD A,#0AH |
| 510 | | JC LSD |
| 511 | | INC R7 |
| 512 | | CPL A |
| 513 | | MOV R5,A |
| 514 | | JMP NSD |
| 515 | LSD: | MOV A,R5 |
| 516 | | MOV R6,A |
| 517 | HUNS: | MOV A,R7 |
| 518 | | CPL A |
| 519 | | ADD A,#0AH |
| 520 | | JC ADD256 |
| 521 | | INC@R0 |
| 522 | | CPL A |
| 523 | | MOV R7,A |
| 524 | | JMP HUNS |
| 525 | ADD256: | JF0 $+4 |
| 526 | | JMP AVOUT |
| 527 | | MOV A, R6 |
| 528 | | ADD A,#06H |
| 529 | | MOV R6,A |
| 530 | | MOVA,R7 |
| 531 | | ADD A,#05H |
| 532 | | MOVR7,A |
| 533 | | MOV A, @R0 |
| 534 | | ADD A, #02H |
| 535 | | MOV @R0,A |
| 536 | | MOV A,R6 |
| 537 | | ADD A,#0F6H |
| 538 | | JNC $+5 |
| 539 | | INC R7 |
| 540 | | MOV R6,A |
| 541 | | CLR C |
| 542 | | MOV A,R7 |
| 543 | | ADD A,#0F6H |
| 544 | | JNC $+5 |
| 545 | | MOV R7,A |
| 546 | | INC @R0 |
| 547 | | CLR C |
| 548 | AVOUT: | SEL RB0 |
| 549 | | MOV A,R4 |
| 550 | | INC A |
| 551 | | RL A |
| 552 | | ADD A,R4 |
| 553 | | ADD A,#24H |
| 554 | | MOV R1,A ;STORE STRESS READING |
| 555 | | MOV R0,#20H |
| 556 | | MOV R7, #03H |

-continued

| | | |
|---|---|---|
| 557 | | MOV A,@R0 |
| 558 | | MOV @R1,A |
| 559 | | DEC R0 |
| 560 | | DEC R1 |
| 561 | | DJNZ R7,$−4 |
| 562 | | DJNZ R4,$+4 |
| 563 | | JMP GEL |
| 564 | | JMP LOAD |
| 565 | RECALL: | ANL P2,#0A0H |
| 566 | | ORL P2,#02H |
| 567 | | MOV A,#0FBH |
| 568 | | MOV T,A |
| 569 | | STRT CNT ;START 5 SEC. TIMER |
| 570 | | JTF $+9 |
| 571 | | IN A,P1 |
| 572 | | ANL A,#0FH |
| 573 | | XRL A,#0AH |
| 574 | | JNZ $+4 |
| 575 | | JMP KEYOUT |
| 576 | | JNI $−11 |
| 577 | | IN A,P1 ;READ MEMORY LOCATION |
| 578 | | ANL A,#0FH |
| 579 | | MOV R4,A |
| 580 | | RL A |
| 581 | | ADD A,R4 |
| 582 | | MOV R4,A |
| 583 | | ADD A,#21H |
| 584 | | MOV R1,A |
| 585 | | MOV R0,#1EH ;LOAD STRESS DATA |
| 586 | | MOV R7,#03H |
| 587 | | MOV A,@R1 |
| 588 | | MOV @R0,A |
| 589 | | INC R0 |
| 590 | | INC R1 |
| 591 | | DJNZ R7,$−4 |
| 592 | | MOV A,R4 ;CALCULATE RPM ADDRESS |
| 593 | | ADD A,#40H |
| 594 | | MOV R1,A |
| 595 | | MOV R0,190 1BH |
| 596 | | MOV R7,#03H |
| 597 | | MOV A,@R1 |
| 598 | | MOV @R0,A |
| 599 | | INC R0 |
| 600 | | INC R1 |
| 601 | | DJNZ R7,$−4 |
| 602 | | CALL DISP |
| 603 | | CALL CLRFIF |
| 604 | | JMP RECALL |
| 605 | STORE: | IN A,P1 |
| 606 | | ANL A,#0FH |
| 607 | | MOV R5,A |
| 608 | | XRL A,#0AH |
| 609 | | JNZ $+4 |
| 610 | | JMP KEYOUT |
| 611 | | JNI STORE |
| 612 | | MOV A,R5 ;CALC STRESS ADDRESS |
| 613 | | RL A |
| 614 | | ADD A,R5 |
| 615 | | MOV R4,A |
| 616 | | ADD A,#23H |
| 617 | | MOV R5,A ;CALCULATE RPM ADDRESS |
| 618 | | MOV A,R4 |
| 619 | | ADD A,#40H |
| 620 | | MOV R4,A |
| 621 | | CALL STODATE ;STORE STRESS DATA |
| 622 | | MOV A,R4 |
| 623 | | MOV R1,A |
| 624 | | MOV R0,#1BH ;STORE RPM DATA |
| 625 | | MOV R3,#03H |
| 626 | | MOV A,@R0 |
| 627 | | MOV @R1, A |
| 628 | | INC R0 |
| 629 | | INC R1 |
| 630 | | DJNZ R3,$−4 |
| 631 | | CALL CLRFIF ;CLEAR FIFO OF 8279 |
| 632 | | JMP KEYOUT |
| 633 | KEYOUT: | STOP TCNT |
| 634 | | JTO $+4 |
| 635 | | JMP $+13 |
| 636 | | JF1 $+9 |
| 637 | | CALL RPM |
| 638 | | CALL STRESS |

-continued

| | | | |
|---|---|---|---|
| 639 | | CALL DISP | |
| 640 | | CPL F1 | |
| 641 | | JMP KYBD | |
| 642 | | CLR F1 | |
| 643 | | JMP KYBD | |
| 644 | | ORG 400H | |
| 645 | OFFADJ: | MOV R0,#7FH | |
| 646 | | CLR A | |
| 647 | | MOV R3,A | |
| 648 | | MOV @R0,A | |
| 649 | | MOV A,#0FEH | |
| 650 | | MOV T,A | |
| 651 | | STRT CNT | ;START 2 SEC. TIMER |
| 652 | | JTF $+4 | |
| 653 | | JMP $−2 | |
| 654 | | STOP TCNT | |
| 655 | CAL: | ANL P2,#0A0H | |
| 656 | | ORL P2,#02H | |
| 657 | | IN A,P1 | |
| 658 | | ANL A,#0FH | |
| 659 | | XRL A,@0AH | |
| 660 | | JNZ ADJUST | |
| 661 | | CALL STRESS | |
| 662 | | CALL DISP | |
| 663 | | JMP CAL | |
| 664 | ADJUST: | MOV A,#0FEH | |
| 665 | | MOV T,A | |
| 666 | | STRT CNT | ;START 2 SCE. TIMER |
| 667 | | JIF $+4 | |
| 668 | | JMP $−2 | |
| 669 | | STOP TCNT | |
| 670 | | ANL P2,#0A0H | |
| 671 | | ORL P2,#04H | |
| 672 | | IN A,P1 | ;READ OFFSET |
| 673 | | MOV R2,A | |
| 674 | | ORL P2,#08H | |
| 675 | | IN A,P1 | |
| 676 | | ANL A,#0FH | |
| 677 | | MOV R0,@7EH | |
| 678 | | MOV @R0,A | |
| 679 | | CALL COMP | |
| 680 | | JZ $+6 | |
| 681 | | MOV A,R2 | |
| 682 | | MOV R3,A | |
| 683 | | JMP ADJUST | |
| 684 | | MOV R1,#7FH | |
| 685 | | MOV A,@R0 | |
| 686 | | JNZ $+6 | |
| 687 | | MOV A,R2 | |
| 688 | | MOV @R1,A | |
| 689 | | JMP $+6 | |
| 690 | | MOV A,R2 | |
| 691 | | ADD A,#80H | |
| 692 | | MOV @R1,A | |
| 693 | | CLR C | |
| 694 | | CLR F1 | |
| 695 | | JMP KYBD | |
| 696 | DISP: | PREP 0F0H, 15H,90H | |
| 701 | | ANL P2,#0EFH | ;SET C/D LOW |
| 702 | | MOV R0,#1BH | |
| 703 | | MOV R2,#06H | |
| 704 | EACH: | MOV A,@P0 | |
| 705 | | ADD A,#TAB7 | |
| 706 | | MOVP3 A,@A | |
| 707 | | OUTL BUS,A | |
| 708 | | INC R0 | |
| 709 | | DJNZ R2,$+3 | |
| 710 | | RETR | |
| 711 | | JMP EACH | |
| 712 | STRESS: | ANL P2,#0A0H | |
| 713 | | ORL P2,#04H | |
| 714 | | MOV R0,#20H | |
| 715 | | IN A,P1 | ;READ LSD AND NSD |
| 716 | | MOV R1,A | |
| 717 | | ORL P2,#08H | ;SET A9 HIGH |
| 718 | | NOP | |
| 719 | | IN A,P1 | ;READ MSD |
| 720 | | ANL A,#0FH | |
| 721 | | MOV @R0,A | |
| 722 | | DEC R0 | |
| 723 | | MOV A,R1 | |
| 724 | | SWAP A | |

-continued

| | | |
|---|---|---|
| 725 | | ANL A,#0FH |
| 726 | | MOV @R0,A ;LOAD DATA TO REGISTER |
| 727 | | DEC R0 |
| 728 | | MOV A,R1 |
| 729 | | ANL A,#0FH |
| 730 | | MOV @R0,A |
| 731 | | CLR C |
| 732 | | MOV R0,#20H |
| 733 | | MOV $1,#03H |
| 734 | | MOV A,@R0 |
| 735 | | ADD A,@0F5H |
| 736 | | JNC 4+4 |
| 737 | | JMP STRESS |
| 738 | | DEC R0 |
| 739 | | DJNZ R1,$−8 |
| 740 | | MOV R0,#7EH |
| 741 | | MOV R1,#7FH |
| 742 | | MOV A,@R1 |
| 743 | | MOV @R0,A |
| 744 | NEWOFF: | MOV R0,#7EH |
| 745 | | MOV A,@R0 |
| 746 | | MOV R1,A |
| 747 | | JNZ $+4 |
| 748 | | JMP ADJOUT |
| 749 | | JB7 NEGOFF |
| 750 | | MOV R0,#20H |
| 751 | | MOV A,@R0 |
| 752 | | XRL A,#0AH |
| 753 | | JZ ADDN |
| 754 | | MOV R0,#1EH |
| 755 | | MOV A,@R0 |
| 756 | | JZ $+8 |
| 757 | | DEC A |
| 758 | | MOV @R0,A |
| 759 | CNTR: | DJNZ R1,$−7 |
| 760 | | JMP ADJOUT |
| 761 | | INC R0 |
| 762 | | MOV A,@R0 |
| 763 | | JZ $+9 |
| 764 | | DEC A |
| 765 | | MOV @R0,A |
| 766 | | DEC R0 |
| 767 | | MOV @R0,#09H |
| 768 | | JMP CNTR |
| 769 | | MOV R0,#20H |
| 770 | | MOV A,@R0 |
| 771 | | JZ $+12 |
| 772 | | DEC A |
| 773 | | MOV @R0,A |
| 774 | | DEC R0 |
| 775 | | MOV @R0,#09H |
| 776 | | DEC R0 |
| 777 | | MOV @R0,#09H |
| 778 | | JMP CNTR |
| 779 | | MOV @R0,#0AH |
| 780 | | JMP ADDN |
| 781 | NEGOFF: | MOV R0,#2 0H |
| 782 | | MOV A,@R0 |
| 783 | | XRL A,#0AH |
| 784 | | JNZ CLRB7 |
| 785 | | MOV R0,#1EH |
| 786 | | MOV A,@R0 |
| 787 | | DEC A |
| 789 | | MOV @R0,A |
| 790 | | ANL A,#0FH |
| 791 | | MOV R1,A |
| 792 | | DJNZ R1,$+4 |
| 793 | | JMP ADJOUT |
| 794 | | MOV R0,#7EH |
| 795 | | MOV A,@R0 |
| 796 | | DEC A |
| 797 | | MOV @R0,A |
| 798 | | MOV R0,#1EH |
| 799 | | MOV A,@R0 |
| 800 | | JNZ $+6 |
| 801 | | MOV R0,#20H |
| 802 | | MOV @R0,#00H |
| 803 | | JMP NEWOFF |
| 804 | CLRB7: | MOV A,R1 |
| 805 | | ANL A,#0FH |
| 806 | | MOV R1,A |
| 807 | ADDN: | MOV R0,#1EH |

-continued

| | | | |
|---|---|---|---|
| 808 | | MOV A,@R0 | |
| 809 | | INC A | |
| 810 | | DA A | |
| 811 | | NOP | |
| 812 | | NOP | |
| 813 | | NOP | |
| 814 | | JB4 $+9 | |
| 815 | | MOV @R0,A | |
| 816 | | DJNZ R1,$+4 | |
| 817 | | JMP ADJOUT | |
| 818 | | JMP ADDN | |
| 819 | | ANL A,#0FH | |
| 820 | | MOV @R0,A | |
| 821 | | INC R0 | |
| 822 | | JMP $−19 | |
| 823 | ADJOUT: | MOV R0,#1EH | |
| 824 | | MOV A,@R0 | |
| 825 | | JNZ $+14 | |
| 826 | | INC R0 | |
| 827 | | MOV A,@R0 | |
| 828 | | JNZ $+10 | |
| 829 | | INC R0 | |
| 830 | | MOV A,@R0 | |
| 831 | | XRL A,#0AH | |
| 832 | | JNZ $+4 | |
| 833 | | MOV @R0,#00H | |
| 834 | | RETR | |
| 835 | RPM: | ANL P2,#0A0H | |
| 836 | | ORL P2,#01H | |
| 837 | | MOV R0,#1BH | |
| 838 | | MOV R7,#03H | |
| 839 | | MOV R1,#10H | ;SET MASK |
| 840 | RPMIN: | IN A,P1 | |
| 841 | | MOV R3,A | |
| 842 | | CPL A | |
| 843 | | ANL A,R1 | |
| 844 | | XRL A,R1 | |
| 845 | | JNZ RPMIN | |
| 846 | | MOV A,R3 | |
| 847 | | ANL A,#0FH | |
| 848 | | MOV @R0,A | |
| 849 | | INC R0 | |
| 850 | | DJNZ R7,$+3 | |
| 851 | | RETR | |
| 852 | | MOV A,R1 | |
| 853 | | RL A | ;ROTATE MASK |
| 854 | | MOV R1,A | |
| 855 | | JMP RPMIN | |
| 856 | COMP: | CLR F1 | |
| 857 | | CLR C | |
| 858 | | MOV A,R2 | |
| 859 | | CPL A | |
| 860 | | ADD A,R3 | |
| 861 | | INC A | |
| 862 | | JNC LTEQ | |
| 863 | | CPL F1 | |
| 864 | | JN $+3 | |
| 865 | | CLR F1 | |
| 866 | LTEQ: | RETR | |
| 867 | ENTER: | MOV A,#93H | |
| 868 | | OUTL P2,A | |
| 869 | | MOV R0,#18H | |
| 870 | | MOV A,@R0 | |
| 871 | | INC R0 | |
| 872 | | SWAP A | |
| 873 | | ADD A,@R0 | |
| 874 | | INC R0 | |
| 875 | | SWAP A | |
| 876 | | OUTL BUS,A | |
| 877 | | MOV A,@R0 | |
| 878 | | OUTL BUS,A | |
| 879 | | CLR A | |
| 880 | | MOV @R0,A | |
| 881 | | DEC R0 | |
| 882 | | MOV @R0,A | |
| 883 | | DEC R0 | |
| 884 | | MOV @R0,A | |
| 885 | | RETR | |
| 886 | MIX: | MOV A,#0F5H | |
| 887 | | MOV T,A | |
| 888 | | STRT CNT | ;START 10 SEC. TIMER |
| 889 | | MOV R0,#1AH | |

| | | -continued | |
|---|---|---|---|
| 890 | | MOV R6,#0D1H | |
| 891 | | MOV R3,#03H | |
| 892 | | MOV A,R6 | |
| 893 | | MOVP3 A,@A | |
| 894 | | MOV @R0,A | |
| 895 | | DEC R0 | |
| 896 | | INC R6 | |
| 897 | | DJNZ R3,$−5 | |
| 898 | | CALL ENTER | |
| 899 | | MOV R0,#1DH | |
| 900 | | IRP X, 9BH,11H | |
| 901 | | MOV @R0,#X | |
| 902 | | DEC R0 | |
| 903 | | ENDM | |
| 908 | | MOV @R0,#12H | |
| 909 | | CALL DISP | |
| 910 | | MOV A,#82H | |
| 911 | | OUTL P2,A | |
| 912 | | JTF $+11 | |
| 913 | | IN A,P1 | |
| 914 | | ANL A,#0FH | |
| 915 | | XRL A,#0AH | |
| 916 | | JZ $+4 | |
| 917 | | JMP $−9 | |
| 918 | | STOP TCNT | |
| 919 | | RETR | |
| 920 | STODAT: | MOV A,R5 | |
| 921 | | MOV R1,A | |
| 922 | | MOV R0,#20H | |
| 923 | | MOV R3,#03H | |
| 924 | | MOV A@R0 | |
| 925 | | MOV @R1,A | |
| 926 | | DEC R0 | |
| 927 | | DEC R1 | |
| 928 | | DJNZ R3,$−4 | |
| 929 | | RETR | |
| 930 | GMESS: | MOV R0,#20H | ;LOAD 'GEL' MESSAGE |
| 931 | | IRP M, OEH,FH | |
| 932 | | MOV @R0,#M | |
| 933 | | DEC R0 | |
| 934 | | ENDM | |
| 939 | | MOV @R0,#10H | |
| 940 | | RETR | |
| 941 | AUMESS: | MOV R0,#20H | ;LOAD 'AU' MESSAGE |
| 942 | | IRP M, OBH,OCH | |
| 943 | | MOV @R0,#M | |
| 944 | | DEC R0 | |
| 945 | | ENDM | |
| 950 | | MOV @R0,#0DH | |
| 951 | | RETR | |
| 952 | CLRFIF: | PREP 0F0H,15H,0C2H | |
| 957 | | RETR | |
| 958 | | ORG 3D1H | |
| 959 | | DB 07H,00H,00H,06H,00H,00H,03H,00H | |
| 960 | | DB 00H,02H,00H,00H,01H,00H,00H,00H | |
| 961 | | DB 06H,00H,00H,03H,00H,00H,01H,05H | |
| 962 | | DB 00H,00H,06H,3FH,06H,5BH,4FH,66H | |
| 963 | | DB 6DH,7DH,07H,7FH,6FH,40H,00H,77H | |
| 964 | | DB 1CH,3DH,79H,38H,76H,06H,50H | |
| 965 | | END | |

Although the presently preferred embodiment of the present invention has been shown and discussed herein, it will be understood that many variations and alternate embodiments of the invention will be apparent to those skilled in the art. For example, other types of optical encoders other than the Gray code encoder may be used to indicate the angular position of the BOB. Furthermore, although the viscometer has been described as being used in connection with drilling fluids in the petroleum industry, it will be understood by those skilled in the art that the invention is applicable as well in measuring rheometric properties of any type of fluid.

What is claimed is:

1. A rotating-cylinder viscometer for measuring the shear stress at a given shear rate of a fluid contained between a rotatable outer cylinder and a rotatable inner cylinder, the inner cylinder rotating in response to forces produced in the fluid by rotation of the outer cylinder, and where the amount of rotation of the inner cylinder is related to the shear stress of the fluid, the viscometer comprising:

(a) a system clock, for providing system clock signals;

(b) a microprocessor unit responsive to said system clock, for inputting and outputting data signals to select the shear rate of rotation of the outer cylinder and to obtain during measurement intervals a plurality of readings of the amount of angular rotation of the inner cylinder at each selected shear rate;

(c) a shear rate controller responsive to said clock and the shear rate selecting data from said microprocessor, for rotating the outer cylinder at a predetermined constant angular velocity;

(d) a position indicator connected to the inner cylinder for rotation therewith, for indicating the angular position of the inner cylinder;

(e) a function selector means connected to said microprocessor, for inputing to said microprocessor the mode of operation for the viscometer, and for inputing the preselected shear rates at which the outer cylinder is to be rotated; and (f) display means responsive to said microprocessor, for displaying both a measured shear stress and the angular velocity of the outer cylinder at which the displayed shear stress was measured, said microprocessor determining from the average angular readings for the plurality of angular position readings of the inner cylinder for each measurement interval when the steady state shear stress has been reached, the steady state shear stress obtaining when the average angular readings for consecutive measurement intervals differ by no more than a predetermined amount.

2. The viscometer of claim 1 wherein the system clock is crystal controlled.

3. The viscometer of claim 1 wherein the shear rate controller comprises:
   (a) a motor, for rotating the outer cylinder;
   (b) a speed encoder connected to the outer cylinder for rotation therewith, said encoder outputting a feedback frequency signal;
   (c) a programmable frequency divider responsive to the shear rate selecting data, for dividing the feedback frequency signal to obtain a phase detector clock signal; and
   (d) a motor drive means responsive to the system clock and the phase detector clock signal, for generating the excitation signal to said motor, whereby the motor speed is controlled in accordance with the shear rate selecting data to obtain a constant frequency for the feedback frequency signal.

4. The viscometer of claim 3 wherein said speed encoder is an optical incremental encoder.

5. The viscometer of claim 3 wherein said motor drive means is enabled by said microprocessor to drive said motor, said means comprising:
   (a) a phase detector responsive to a system clock signal and the phase detector clock signal, for generating a phase error signal indicative of the phase between the phase detector clock signal and the clock signal; and
   (b) an amplifier, for generating the motor excitation signal from the phase error signal thereby causing said motor to rotate.

6. The viscometer of claim 3 wherein said motor is a DC-motor of the ironless armature type.

7. The viscometer of claim 3 wherein said programmable frequency divider is a divide-by-N counter.

8. The viscometer of claim 1 wherein said position indicator is an absolute value shaft encoder that outputs a code indicative of the absolute value of the shaft angle.

9. The viscometer of claim 8 wherein the code is a Gray code.

10. The viscometer of claim 9 further comprising a code converter for converting the Gray code to a BCD code.

11. The viscometer of claim 10 wherein said code converter is a read-only memory containing BCD code words that are outputted in response to memory addresses provided by the Gray code output of said absolute value shaft encoder.

12. The viscometer of claims 1 or 8 wherein the predetermined amount of angular difference between the average angular readings of consecutive measurement intervals is ±1°.

13. The viscometer of claim 1 wherein said function selector means comprises:
   (a) a keyboard having a plurality of keys including keys for generating numeric data, for generating digital code words in response to the actuation of the keys; and
   (b) an interface, for interfacing the digital code words to said microprocessor, said interface generating an interrupt strobe when a numeric key is depressed.

14. A method of obtaining the shear stress of a fluid at a selected shear rate speed using a rotating-cylinder viscometer having rotatable inner and outer concentric cylinders comprising the steps of:
   (a) mixing the fluid by rotating the outer cylinder at a high speed;
   (b) rotating the outer cylinder at the selected shear rate speed;
   (c) determining a current average value for the angular position of the inner cylinder from a predetermined number of position measurements taken at a predetermined sample rate, the angular position of the inner cylinder having random fluctuation about a position;
   (d) obtaining the difference between the current average value and the last obtained average value;
   (e) repeating steps (c) through (e) if the difference is greater than a predetermined number of degrees, the current average value becoming the last obtained average value for the next steady state determination; and
   (f) reporting the current average value as the measured shear stress if the difference is less than the predetermined number of degrees.

15. The method of claim 14 wherein the step of mixing the fluid occurs at a speed at least as high as the selected shear rate speed at which the shear stress is to be measured.

16. The method of claim 14 wherein the predetermined sample rate is at least twice the rate of the fluctuation in the angular position of the inner cylinder.

17. The method of claim 16 wherein the predetermined number of degrees is ±1 degree.

18. The method of claim 14 further including the steps of:
   (a) determining the angular offset position of the inner cylinder at zero shear rate; and
   (b) correcting all angular position measurements of the inner cylinder by the amount of the zero rate offset.

19. A method of obtaining the steady state shear stress of a fluid at a selected shear rate speed using a rotating-cylinder viscometer in which the fluid is contained between a rotatable outer cylinder and a spring loaded rotatable inner cylinder, the inner cylinder rotating in response to the torque produced by the rotation of the outer cylinder in the fluid whereby the angular rotation of the inner cylinder is indicative of the shear stress of the fluid; the method comprising the steps of:
   (a) mixing the fluid by rotating the outer cylinder at a speed at least as high as the selected shear rate speed at which the shear stress is to be measured for a first predetermined interval of time;

(b) rotating the outer cylinder at the selected shear rate speed for a second predetermined interval of time;

(c) determining a current average value for the angular position of the inner cylinder from a predetermined number of position measurements taken over a third predetermined time interval;

(d) obtaining the difference between the current average value and the last obtained average value;

(e) repeating steps (b) through (e) if the difference is greater than a predetermined number of degrees, the current average value becoming the last obtained average value for the next steady state determination; and (f) reporting the current average value as the measured shear stress if the difference is less than the predetermined number of degrees.

20. A method of obtaining the shear stress profile of a fluid for various preselected shear rate speeds using a rotating-cylinder viscometer having rotatable inner and outer concentric cylinder comprising the steps of:

(a) mixing the fluid by rotating the outer cylinder at a high speed;

(b) rotating the outer cylinder at a current shear rate speed;

(c) determining a current average value for the angular position of the inner cylinder from a position measurements taken at a predetermined sample rate, the angular position of the inner cylinder having random fluctuations about a position;

(d) obtaining the difference between the current average value and the last obtained average value, the current average value becoming the last obtained average value for the next difference determination;

(e) repeating steps (c) through (e) if the difference is greater than a predetermined number of degrees;

(f) storing the current average value as the measured shear stress if the difference is less than the predetermined number of degrees; and (g) repeating steps (c) through (g) until the shear stress at each of the preselected shear rate speeds has been measured thereby obtaining the shear stress profile of the fluid.

21. The method of claim 20 wherein the step of mixing the fluid occurs at a speed at least as high as the highest preselected shear rate speed at which the shear stress is to be measured.

22. The method of claim 20 wherein the predetermined sample rate is at least twice the rate of the fluctuations in the angular position of the inner cylinder.

23. The method of claim 20 wherein the predetermined number of degrees is ±1 degree.

24. The method of claim 20 further including the steps of:

(a) determining the angular offset position of the inner cylinder at zero shear rate; and (b) correcting all angular position measurements of the inner cylinder by the amount of the zero rate offset.

25. The method of claim 23 or 24 wherein the method further includes the steps of:

(a) rotating the outer cylinder at 3 revolutions per minute;

(b) measuring the maximum shear stress reading that occurs during one revolution of the outer cylinder;

(c) repeating steps (a) and (b) after a predetermined time delay.

26. A method of obtaining a shear stress profile of a fluid for various preselected shear rate speeds using a rotating-cylinder viscometer in which the fluid is contained between a rotatable outer cylinder and a spring loaded rotatable inner cylinder, the inner cylinder rotating in response to the torque produced by the rotation of the outer cylinder in the fluid whereby the angular rotation of the inner cylinder is indicative of the shear stress of the fluid the method comprising the steps of:

(a) mixing the fluid by rotating the outer cylinder at a speed at least as high as the highest shear rate speed at which a shear stress is to be measured for a first predetermined interval of time;

(b) selecting one of the preselected shear rate speeds as the current shear rate;

(c) rotating the outer cylinder at the current shear rate speed for a second predetermined interval of time;

(d) determining a current average value for the angular position of the inner cylinder from position measurements taken at a predetermined sample rate over a third predetermined time interval, the angular position of the inner cylinder having random fluctuations about a position over a third predetermined time interval;

(e) obtaining the difference between the current average value and the last obtained average value, the current average value becoming the last obtained average value for the next difference determination;

(f) repeating steps (c) through (f) if the difference is greater than a predetermined number of degrees;

(g) storing the current average value as the measured shear stress if the difference is less than the predetermined number of degrees; and (h) repeating steps (b) through (h) until the shear stress at each of the preselected shear rate speeds has been measured, thereby obtaining the shear stress profile of the fluid.

27. A microprocessor controlled rotating-cylinder viscometer for measuring the steady state shear stress of a fluid located between two coaxially aligned rotatable cylinders in which an outer cylinder is rotated at preselected rates and an inner cylinder is rotated from its zero rate position in response thereto, the viscometer comprising:

(a) means for rotating the outer cylinder at a constant preselected rate;

(b) a shaft encoder connected to the inner cylinder for encoding the angular position of the inner cylinder with respect to the zero rate reference position, the steady state angular position of the inner cylinder for a constant angular rate of the outer cylinder being indicative of the shear stress of the fluid located therebetween; and (c) a programmed microprocessor unit programmed to select the shear rate of rotation of the outer cylinder, and to repetitively obtain at each rate a plurality of readings of the angular position of the inner cylinder during measurement intervals, said processor unit determining the steady state shear stress from average readings of the plurality of angular positions of the inner cylinder determined for each measurement interval, the steady state shear stress obtaining when the average angular positions of the inner cylinder between successive measurement intervals differs by no more than a predetermined value.

28. The viscometer of claim 27 wherein the predetermined value of angular difference is ±1°.

29. The viscometer of claim 27 wherein said shaft encoder is an absolute value shaft encoder for indicating the true angular position of the inner cylinder.

30. The viscometer of claim 27 wherein said rotating means comprises:
(a) a motor responsive to a driving signal, for rotating the outer cylinder;
(b) a speed encoder connected to the outer cylinder for rotation therewith, said encoder outputting a feedback frequency signal;
(c) a programmable frequency divider response to the microprocessor, for dividing the feedback frequency signal to obtain a phase detector clock signal;
(d) a phase detector responsive to said microprocessor and the phase detector signal, for generating a phase error signal indicative of the speed error between the selected shear rate and the actual rate of rotation of the outer cylinder; and
(e) an amplifier responsive to the phase error signal for generating the drive signal to said motor, whereby the motor speed is controlled in accordance with the selected shear rate from said microprocessor.

31. The viscometer of claim 30 wherein said speed encoder is an optical incremental encoder.

32. The viscometer of claims 30 or 31 wherein said motor is a DC-motor of the ironless armature type.

* * * * *